United States Patent [19]

Peterson et al.

[11] Patent Number: 5,062,714

[45] Date of Patent: Nov. 5, 1991

[54] APPARATUS AND METHOD FOR PATTERN RECOGNITION

[75] Inventors: Steven H. Peterson, Wyoming; Timothy R. Friend, Jenison, both of Mich.

[73] Assignee: X-Rite, Incorporated, Grandville, Mich.

[21] Appl. No.: 478,475

[22] Filed: Feb. 12, 1990

[51] Int. Cl.[5] .............................................. G01J 3/51
[52] U.S. Cl. .................................... 356/406; 356/407; 356/419; 356/425; 356/73; 364/526
[58] Field of Search ............... 356/402, 406, 407, 416, 356/418, 419, 425, 73; 250/226; 364/525, 526

[56] References Cited

U.S. PATENT DOCUMENTS

| | | |
|---|---|---|
| 2,287,322 | 6/1942 | Nelson . |
| 3,814,932 | 6/1974 | Anati et al. .......................... 250/226 |
| 3,995,958 | 12/1976 | Pfahl et al. . |
| 4,165,180 | 8/1979 | Failes .................................. 356/310 |
| 4,239,393 | 12/1980 | Tobias .................................. 356/407 |
| 4,310,248 | 1/1982 | Meredith ............................. 356/402 |
| 4,334,241 | 6/1982 | Kashioka et al. .................... 358/107 |
| 4,349,279 | 9/1982 | Jung .................................... 356/402 |
| 4,402,611 | 9/1983 | Yuasa .................................. 356/405 |
| 4,414,635 | 11/1983 | Gast et al. ........................... 356/526 |
| 4,417,818 | 11/1983 | Weisner ............................... 356/404 |
| 4,474,470 | 10/1984 | Brandt et al. ........................ 356/402 |
| 4,488,245 | 12/1984 | Dalke et al. ......................... 364/526 |
| 4,488,808 | 12/1984 | Kato . |
| 4,494,875 | 1/1985 | Schramm et al. .................... 356/402 |
| 4,630,225 | 12/1986 | Hisano ................................. 356/394 |
| 4,654,794 | 3/1987 | O'Brien ............................... 364/413 |
| 4,671,661 | 6/1987 | Ott ....................................... 356/402 |
| 4,720,870 | 1/1988 | Billiotte et al. ....................... 382/8 |
| 4,771,468 | 9/1988 | Batchelder et al. .................. 382/8 |
| 4,773,761 | 9/1988 | Sugiyama et al. ................... 356/405 |
| 4,834,541 | 5/1989 | Yamaba ............................... 356/406 |
| 4,849,914 | 7/1989 | Medioni et al. ..................... 364/526 |

Primary Examiner—F. L. Evans
Attorney, Agent, or Firm—Varnum, Riddering, Schmidt & Howlett

[57] ABSTRACT

A densitometer apparatus (210) is disclosed and is adapted to provide color density measurements of object samples. The densitometer apparatus (210) comprises a source light (578) for projecting light toward an object sample comprising a control strip (588, 620). A reflection optics assembly (576) is adapted to measure light density reflected from the object sample, when the object sample is in the form of a paper control strip. A transmission optics assembly (618) is adapted to measure transmission density of light rays projected through the object sample, when the object sample is in the form of a film control strip. A motor assembly (426) automatically moves the object sample (588,620) through the apparatus (210) adjacent the source light (578). Pattern definition data is prestored in memory of the apparatus (210). When control strips (588, 620) to be analyzed are "read" through the apparatus (210), a pattern recognition process is employed to compare strip color patches with the prestored data, so as to determine whether the control strip "matches" the pattern definition. The pattern definition data is stored so as to define "regions" where dimensional, positional and spectral color patch properties are within predetermined tolerances. An initial step of the pattern recognition process is to scan measured data representative of the control strip and assign regions. Comparisons of the pattern definition region data and measured control strip region data are then performed to determine whether an appropriate "match" has been obtained.

40 Claims, 17 Drawing Sheets

APPARATUS AND METHOD FOR PATTERN RECOGNITION

BACKGROUND OF THE INVENTION

1. Field of the Invention.

The invention relates to apparatus and methods associated with color technology and, more particularly, to pattern recognition apparatus and methods for comparing data representative of measured patterns with data representative of reference or predefined patterns.

2. Description of Related Art

It is well known that the term "color" as applied to electromagnetic radiation represents in part the relative energy distribution of radiation within the visible spectrum. That is, light providing a stimulus to the human eye, and having a particular energy distribution, may be perceived as a substantially different color than light of another energy distribution. Concepts relating to the characteristics of color and light waves are the subject of numerous well-known texts, such as *Principles of Color Technology*, Meyer, Jr. and Saltzman (Wiley 1966) and *The Measurement of Appearance*, Hunter and Harold (Wiley 2nd Ed. 1987).

In recent years, the capability of maintaining the "quality of color" has been of significant importance in various industries such as, for example, the fields of graphic arts, photography and color film processing. For purposes of performing sample testing and other activities in furtherance of maintaining color quality, it is necessary to first determine an appropriate means for "measuring" and "describing" color. A substantial amount of research has been performed during the past 50 years with respect to appropriate methods and standards for color measurement and description.

For purposes of describing color, and from a purely "physical" point of view, the production of color requires three things: a source of light; an object to be illuminated and a means for perceiving the color of the object. The means for perceiving the color can be the human eye and brain or, alternatively, electrical and electromechanical apparatus such as a photosensitive detector and associated auxiliary devices utilized for detecting light. In general, it is desirable to provide a means for measuring color so as to assess the manner in which an image will appear to a human observer, or the manner in which an image will perform in a photographic or other type of reproduction printing operation.

Although human perception and interpretation of color can be useful, reliance on such perception and interpretation can be highly subjective. That is, human nature may cause one person's perception of the color of a particular object to be substantially different from the perception of another. In addition, eye fatigue, age and other physiological factors can influence color perception. Further, visual human perception is often insufficient for color description. For example, certain object samples may be visually perceived under one light source as substantially "matching", and yet may actually have very different spectral characteristics and may be perceived as "nonmatching" under another light source. In view of the foregoing, it is desirable to employ color measurement and description techniques which are objective in nature, and capable of differentiating among object samples having different color characteristics.

Various devices have been developed and are widely utilized to measure and quantitatively describe color characteristics of object samples. Many of these devices provide measurements related to the spectral characteristics of the samples. Described simplistically, when light is directed onto an object sample to be measured for color, the object may absorb a portion of the light energy, while correspondingly passing through or reflecting (if the object is opaque) other portions of the light. The color characteristics of the object sample will depend in part on the spectral characteristics of the object. That is, the effect of an object on light can be described by its spectral transmittance or reflectance curves (for transparent or opaque materials, respectively). These spectral characteristic curves indicate the fraction of the source light at each wavelength transmitted by or reflected from the materials. Such curves are a means for describing the effect of an object on light in a manner similar to the use of a spectral energy distribution curve for describing the characteristics of a source of light. Instruments utilized for generating such spectral characteristic curves are typically referred to as spectrophotometers.

In accordance with conventional optical physics, it is known that the proportion of light incident to an object sample and absorbed by such a sample is independent of the light intensity. Accordingly, a quantitative indication of the spectral characteristics of an object sample can be defined as the "transmittance" or "reflectance" of the sample. That is, the transmittance of a substantially transparent object can be defined as the ratio of power transmitted over light power incident to the sample. Correspondingly, for an opaque object sample, the reflectance can be defined as the ratio of power reflected from the object over the incident light power.

For collimated light, these ratios can be expressed in terms of intensities, rather than power. Furthermore, because of the nature of transmittance/reflectance and the optical characteristics of the human eye, it is advantageous to express these ratios in logarithmic form. Accordingly, one parameter widely used in the field of color technology for obtaining a quantitative measurement or "figure of merit" is typically characterized as optical "density." The optical density of an object sample is typically defined as follows:

$$\text{Optical Density} = D = -\log_{10} T \text{ or } -\log_{10} R \quad \text{(Equation 1)}$$

where T represents transmittance of a transparent object and R represents reflectance of an opaque object. In accordance with the foregoing, if an object sample absorbed 90% of the light incident upon the sample, and the object were opaque, the reflectance would ideally be 10%. The density of such a sample would then be characterized as unity. Correspondingly, if 99.9% of the light were absorbed, the reflectance would be 0.1% and the density would be 3. Similarly, the density of an "ideal" object reflecting 100% of the light incident upon the object would be 0.

To provide a relative measurement of color, it is possible to utilize the principles of optical density, without requiring measurement or knowledge of the absolute values of total incident light intensity or reflectance. That is, for example, it is possible to obtain relative color measurements among a series of object samples by utilizing a particular geometric configuration of light, object sample and reflectance or transmittance detector for each measurement, and standardizing the measurements in some desired manner.

In brief summary, optical density is a measurement of the modulation of light or other radiant flux by an object sample, such as a given area of a photographic print. Density measurements provide a means to assess the manner in which an image will appear to a human observer, or the way an image will perform in a film processing operation. Density measurements can be utilized to produce sensitometric curves to evaluate various printing and reproduction characteristics, as well as utilization to control various photographic operations, such as film processing.

For purposes of measuring optical densities, it is well known to employ a device typically characterized as a "densitometer." These densitometers are often categorized as either "reflection" densitometers, employed for optical density measurements of opaque objects, or are otherwise characterized as "transmittance" densitometers. Transmittance densitometers are employed for determining spectral characteristics of various non-opaque materials.

Densitometers are utilized in various industries for performing a variety of functions. For example, densitometers can be conveniently employed in color film processing applications. Processes associated with these applications will be described in greater detail in subsequent paragraphs herein.

To assist in describing the principles of densitometer apparatus in which concepts of the present invention may be employed, FIG. 1 illustrates a simplified schematic representation of a known reflection densitometer configuration 100. A configuration of this type is described in detail in the commonly assigned and currently pending U.S. Pat. Application Ser. No. 534,205, filed June 7, 1990, which is a continuation of commonly assigned U.S. Patent Application Ser. No. 105,424, filed Oct. 5, 1987 and now abandoned. Densitometer apparatus of the type shown in FIG. 1 are characterized as reflection densitometers, and utilized to provide color density measurements of opaque materials as previously described.

Referring specifically to FIG. 1, and to numerical references therein, the densitometer apparatus 100 includes a light source unit 102 having a source light 104. With respect to optical density measurements in photography, color film processing, and other industrial fields, various standards have been developed for densitometer light source illuminants. For example, densitometer light source standards have previously been described in terms of a tungsten lamp providing an influx from a lamp operating at a Planckian distribution of 3000° K. Other suggested standards have been developed by the American National Standards Institute ("ANSI") and the International Organization for Standardization ("ISO"). These source light densitometer standards are typically defined in terms of the spectral energy distribution of the illuminant. The source light 104 preferably conforms to an appropriate standard and can, for example, comprise a filament bulb meeting a standard conventionally known in the industry as 2856K ANSI. Power for the source light 104 and other elements of the densitometer apparatus 100 can be provided by means of conventional rechargeable batteries or, alternatively, interconnection to AC utility power.

The source light 104 projects light through a collimating lens 106 which serves to focus the electromagnetic radiation from the source light 104 into a narrow collimated beam of light rays. Various types of conventional and well-known collimating lenses can be employed. The light rays transmitted through the collimating lens 106 project through an aperture 108. The dimensions of the aperture 108 will determine the size of the irradiated area of the object sample under test.

Various standards have been defined for preferable sizes of the irradiated area. Ideally, the aperture 108 is of a size such that the irradiance is uniform over the entire irradiated area. However, in any physically realizable densitometer arrangement, such uniform irradiance cannot be achieved. Current standards suggest that the size of the irradiated area should be such that irradiance measured at any point within the area is at least 90% of the maximum value. In addition, however, aperture size is typically limited to the size of the color bar or color patch area to be measured, and is also sized so as to reduce stray light.

The light rays emerging from the aperture 108 (illustrated as rays 110 in FIG. 1) are projected onto the irradiated area surface of an object sample 112 under test. The sample 112 may be any of numerous types of colored opaque materials. For example, in the printing industry, the sample 112 may be an ink-on-paper sample comprising a portion of a color bar at the edge of a color printing sheet. Further, with respect to the illustrative embodiment of a densitometer apparatus employing the principles of the invention as described in subsequent paragraphs herein, the sample 112 may be a control strip employed in the color film processing industry.

As the light rays 110 are projected onto the object sample 112, electromagnetic radiation shown as light rays 114 will be reflected from the sample 112. Standard detection configurations have been developed, whereby reflected light is detected at a specific angle relative to the illumination light rays 110 projected normal to the plane of the object sample 112. More specifically, standards have been developed for detection of reflected light rays at an angle of 45° to the normal direction of the light rays 110. This angle of 45° has become a standard for reflectance measurements, and is considered desirable in that this configuration will tend to maximize the density range of the measurements. In addition, however, the 45° differential also represents somewhat of a relatively normal viewing configuration of a human observer (i.e. illumination at a 45° angle from the viewer's line of sight).

For purposes of providing light detection, a spectral filter apparatus 116 is provided. The filter apparatus 116 can include a series of filters 118, 120 and 122. The filters 118, 120 and 122 are employed for purposes of discriminating the cyan, magenta and yellow spectral responses, respectively. That is, each of the filters will tend to absorb light energy at frequencies outside of the bandwidth representative of the particular color hue of the filter. For example, the cyan filter 118 will tend to absorb all light rays, except for those within the spectral bandwidth corresponding to a red hue. By detecting reflected light rays only within a particular color hue bandwidth, and obtaining an optical density measurement with respect to the same, a "figure of merit" can be obtained with respect to the quality of the object sample coloring associated with that particular color hue.

It is apparent from the foregoing that the actual quantitative measurement of color density or color reflectance is dependent in substantial part on the spectral transmittance characteristics of the filters. Accordingly, various well-known standards have been developed with respect to spectral characteristics of densitometer filters. For example, one standard for densitometer filters is known as the ANSI status T color response. The spectral response characteristics of filters meeting this standard are relatively wide band (in the range of 50–60 namometers bandwidth) for each of the cyan, magenta and yellow color hues. Other spectral response characteristic standards include, for example, what is known as G-response, which is somewhat similar to status T, but is somewhat more sensitive with respect to yellow hues. An E-response represents a European response standard.

Although the filters 118, 120 and 122 are illustrated in the embodiment shown in FIG. 1 as the cyan, magenta and yellow color shades, other color shades can clearly be employed. These particular shades are considered somewhat preferable in view of their relative permanence, and because they comprise the preferred shades for use in reflection densitometer calibration. However, it is apparent that different shades of red, blue and yellow, as well as entirely different colors, can be utilized with the densitometer apparatus 100.

The spectral filters 118, 120 and 122 may not only comprise various shades of color, but can also be one of a number of several specific types of spectral response filters. For example, the filters can comprise a series of conventional Wratten gelatin filters and infrared glass. However, various other types of filter arrangements can also be employed.

The spectral filters 118, 120 and 122 are preferably positioned at a 45° angle relative to the normal direction from the plane of the object sample 112 under test. In the particular example shown in FIG. 1, each of these filters is maintained stationary and utilized to simultaneously receive light rays reflected from the object sample 112. Further, although the particular example illustrated in FIG. 1 may include a stationary object sample 112, the example embodiment of a densitometer apparatus employing principles of the invention as described in subsequent paragraphs herein can include an object sample which is continuously moving relative to the spectral filter arrangement. In such an instance, the actual spectral filter measurements may be obtained simultaneously or, alternatively, in sequence.

As further shown in FIG. 1, the portion of the reflected light rays 114 passing through the filters 118, 120 and 122 (shown as light rays 124, 126 and 128, respectively) impinge on receptor surfaces of photovoltaic sensor cells. The sensor cells are illustrated in FIG. 1 as sensors 132, 134 and 136 associated with the spectral filters 124, 126 and 128, respectively. The sensors 132, 134 and 136 can comprise conventional photoelectric elements adapted to detect light rays emanating through the corresponding spectral filters. The sensors are further adapted to generate electrical currents having magnitudes proportional to the intensities of the sensed light rays. As illustrated in FIG. 1, electrical current generated by the cyan sensor 132 in response to the detection of light rays projecting through the filter 118 is generated on line pair 138. Correspondingly, electrical current generated by the magenta sensor 134 is applied to the line pair 140, while the electrical current generated by the yellow sensor 136 is applied as output current on line pair 142. Photoelectric elements suitable for use as sensors 136, 138 and 140 are well-known in the art, and various types of commercially-available sensors can be employed.

The magnitude of the electrical current on each of the respective line pairs will be proportional to the intensity of the reflected light rays which are transmitted through the corresponding spectral filter. These light rays will have a spectral distribution corresponding in part to the product of the spectral reflectance curve of the object sample 112, and the spectral response curve of the corresponding filter. Accordingly, for a particular color shade represented by the spectral response curve of the filter, the magnitude of the electrical current represents a quantitative measurement of the proportional reflectance of the object sample 112 within the frequency spectrum of the color shade.

As further shown in FIG. 1, the sensor current output on each of the line pairs 138, 140 and 142 can be applied as an input signal to one of three conventional amplifiers 144, 146 and 148. The amplifier 144 is responsive to the current output of cyan sensor 132 on line pair 138, while amplifier 146 is responsive to the sensor current output from magenta sensor 134 on line pair 144. Correspondingly, the amplifier 148 is responsive to the sensor current output from yellow sensor 136 on line pair 142. Each of the amplifiers 144, 146 and 148 provides a means for converting low level output current from the respective sensors on the corresponding line pairs to voltage level signals on conductors 150, 152 and 154, respectively. The voltage levels of the signals on their respective conductors are of a magnitude suitable for subsequent analog-to-digital (A/D) conversion functions. Such amplifiers are well known in the circuit design art, and are commercially available with an appropriate volts per ampere conversion ratio, bandwidth and output voltage range. The magnitudes of the output voltages on lines 150, 152 and 154 again represent the intensities of reflected light rays transmitted through the corresponding spectral filters.

Each of the voltage signal outputs from the amplifiers can be applied as an input signal to a conventional multiplexer 156. The multiplexer 156 operates so as to time multiplex the output signals from each of the amplifiers 144, 146 and 148 onto the conductive path 158. Timing for operation of the multiplexer 156 can be provided by means of clock signals from master clock 160 on conductive path 162. During an actual density measurement of an object sample, the densitometer 100 will utilize a segment of the resultant multiplexed signal which sequentially represents a voltage output signal from each of the amplifiers 144, 146 and 148.

The resultant multiplexed signal generated on the conductive path 158 is applied as an input signal to a conventional A/D converter 164. The A/D converter 164 comprises a means for converting the analog multiplexed signal on conductor 158 to a digital signal for purposes of subsequent processing by central processing unit (CPU) 166. The A/D converter 164 is preferably controlled by means of clock pulses applied on conductor 168 from the master clock 160. The clock pulses operate as "start" pulses for performance of the A/D conversion. The A/D converter 164 can be any suitable analog-to-digital circuit well known in the art and can, for example, comprise 16 binary information bits, thereby providing a resolution of 65K levels per input signal.

The digital output signal from the A/D converter 164 can be applied as a parallel set of binary information bits on conductive paths 170 to the CPU 166. The CPU 166 can provide several functions associated with operation of the densitometer apparatus 100. In the embodiment described herein, the CPU 166 can be utilized to perform these functions by means of digital processing and computer programs. In addition, the CPU 166 can be under control of clock pulses generated from the master clock 160 on path 172. However, a number of the functional operations of CPU 166 could also be provided by means of discrete hardware components.

In part, the CPU 166 can be utilized to process information contained in the digital signals from the conductive paths 170. Certain of this processed information can be generated as output signals on conductive path 176 and applied as input signals to a conventional display circuit 178. The display circuit 178 provides a means for visual display of information to the user, and can be in the form of any one of several well-known and commercially-available display units.

In addition to the CPU 166 receiving digital information signals from the conductive paths 170, information signals can also be manually input and applied to the CPU 166 by means of a manually-accessible keyboard circuit 180. The user can supply "adjustments" to color responses by means of entering information through the keyboard 180. Signals representative of the manual input from the keyboard 180 are applied as digital information signals to the CPU 166 by means of conductive path 182.

The previously described concepts of densitometry can be of primary significance in fields such as the color photography and processing industry. For purposes of illustration and example, the color photograph processing procedure can be described as comprising a series of three process steps. First, the exposed roll or strip of color film is subjected to a process for producing a series of "negatives" from the exposed film roll or strip. This process is well known in the photography industry and can essentially be characterized as a chemical process for producing a series of negative images, in which the "brightness" values of the photograph subject are reproduced so that the lightest areas are shown as the darkest areas.

Secondly, the color photography development process comprises a step wherein the photographic negative is utilized with photographic paper in a manner such that the photographic paper is subjected to exposure from the negative. In this process, the film base and exposure times can be varied as appropriate to achieve the proper color balance on the exposed paper. Finally, the exposed film paper is subjected to a chemical process for generating the finished photographic prints.

Each of the aforedescribed processes is relatively conventional and well known in the photographic industry. However, each of these processes requires the "setting" of various control variables on the equipment utilized to perform the processes. For example, the processes associated with producing the negatives and processing the exposed paper comprise chemical processes whereby color chemistry variables may be adjusted so as to produce negatives and finished prints of appropriate colors. Correspondingly, the process step whereby the photographic print paper is exposed from the negatives will also have various variables associated with the process. For example, this particular process will involve the use of "white" light sources and spectral filters for exposing the negative onto the photographic paper in differing manners. Further, a variable associated with this particular process comprises the exposure times for the exposure of the negative onto the photographic paper. As an example, the negative may be exposed onto the paper through an unfiltered white light source for a certain predetermined period of time. However, if such an exposure is not producing an appropriate color balance, filters may be employed whereby only a particular color (i.e. energy from a portion of the color spectrum) of the white light source is exposed onto the photographic paper for some portion of the entirety of the exposure time. This type of operation is typically referred to as a "balancing" of the color.

With respect to the final step of the photographic development process, i.e. the processing of the exposed photographic paper to produce the final photographic prints, a number of variables are also associated with this type of process. For example, the chemistry of the film bath may be varied through the use of various chemical mixtures so to again achieve correct print processing to maintain appropriate photograph colors.

Various methods and equipment have been developed for providing the photograph developers with a means for measuring the "quality" of the individual process steps associated with the entirety of the photograph development process. In particular, it is relatively well known to utilize densitometers to measure optical transmittance density of processed negatives and optical reflectance density of processed photographic paper to determine if the equipment is producing appropriate color balances. However, when measuring color densities to determine the quality of the film processing, it is desirable to compare such density measurements against "ideal" processed materials. Accordingly, the field of film processing readily lends itself to the comparison of color densities of materials processed by the operator's own equipment against reference standards.

Further, however, the photographic industry does not have any ideal standards related to each of the process steps associated with film development. Additionally, optimum color densities of processed materials may vary dependent upon the particular type of film or paper material being utilized by the operator. Accordingly, manufactures of film processing equipment and materials will provide their own individual reference standards for purposes of optimizing the film development process.

More specifically, it is known in the field of color photograph film processing to utilize "strips" of negative and paper materials to periodically test the quality of the operator's own processing equipment. In addition, manufacturers also provide "reference" strips of materials which can be characterized as processed strips comprising "ideal" processing of the manufacturers' materials.

To further illustrate the use of the reference strips and the control strips, a strip commonly identified as the Kodak C-41 strip is illustrated in FIG. 2. The C-41 strip is manufactured by Eastman Kodak Company. The strip illustrated in FIG. 2 is identified as strip 200 and comprises a film negative having various color hues associated with the negative. When the film development equipment operator is utilizing film negatives manufactured by Eastman Kodak, the operator will obtain a referenced film strip and a series of control strips having a configuration as shown in FIG. 2. The reference strip can be characterized as a negative which has been fully processed by the manufacturer. The negative is considered to comprise a series of color patches having the "ideal" color hues for the negative processing. Correspondingly, the control strips provided by the manufacturer will be a series of unprocessed strip negatives. The principal use and concept associated with these strips is to allow the operator to adjust the film negative processor so that the color densities of control strips processed by the negative processor will optimally "match" color densities of the reference strip.

To perform the operation of measuring the quality of the negative processing, a densitometer can first be used to measure the transmission densities of the reference strip. Again, these transmission densities represent ideal densities to be achieved by the equipment negative processor. Although it would be possible to utilize color density values somehow identified on the reference strip, such values may not comprise the same density values which will be measured by the operator's own densitometer. That is, the "absolute values" of the color densities are not particularly important. Instead, the quality of the film negative processing by the operator's equipment will be indicated by the comparison of the measured color densities of a processed control strip relative to the measured color densities of the reference strip. Because densitometers may vary in their measurement readings from one device to another, it is of primary importance that the color densities for the reference strip and the control strips be measured by the same device.

After measurement of the color densities associated with the reference strip, a control strip having a similar configuration to the strip 200 is processed by the operator, using the operator's own equipment. Following processing of the film negative, the processed control strip is now measured to determine the color densities associated therewith. The differences in the relative color density measurement values between the reference strip and the processed control strip will indicate to the operator whether any adjustments in the film negative processing operation are required. Indeed, many of the primary manufacturers will provide written "trouble shooting" manuals indicating the types of adjustments which may be necessary in view of certain types of differences between the density measurements associated with the processed control strip and the density measurements associated with the reference strip. As an example, the operator may find that the "green" density value for the processed control strips is continuously lower than the green density value for the reference strip. The written trouble shooting manuals may then provide suggestions as to the particular activities which may be undertaken by the operator with respect to adjustment of the negative processor equipment.

With respect to adjustments to the processing equipment associated with the exposure of the negative onto the photographic paper, manufacturers provide reference and control strips commonly known as "print balance" strips. Such a print balance control strip is illustrated in FIG. 3 as print balance strip 202. As shown in FIG. 3, the strip comprises three color patches identified as the "over", "normal" and "under" patches. These patches comprise color densities which may be expected with respect to photographic paper that has been overexposed, normal and underexposed, respectively. The print balance control strips are employed to maintain a printing balance during the exposure of a negative onto the photographic paper. Again, in a manner similar to the processing step associated with processing the negative, the manufacturers will provide a print balance reference strip, in addition to a series of unprocessed print balance strips. The operator would again measure the color densities of the patches of the reference strip representative of overexposure, normal processing and underexposure. These color density values would then be compared against the actual color density values of materials processed by the operator's own equipment. These measurements can assist the operator in adjusting exposure times and filtering so as to achieve a proper color balance in exposing the negative onto the photographic paper.

With respect to the third step of the overall development process, i.e. the processing of the exposed photographic paper to obtain the final photographic prints, the manufacturers provide further reference and control strips to adjust variables in the processing step. A control strip commonly identified as the Kodak EP-2 strip (manufactured by the Eastman Kodak Company) is illustrated as control strip 204 in FIG. 4. Again, the operator would be provided with the reference strip having the "ideal" color densities. That is, the reference strip would comprise a strips of photographic print having the ideal color densities for this processing step. The operator would measure these reflection color densities and compare the densities against control strips processed by the operator's own equipment. Manufacturers provide written trouble shooting manuals for this processing step in a manner similar to the materials provided for the production of the film negatives. That is, differences in the measured color densities will typically indicate certain problems associated with this step of the film processing. As an example, a relatively substantial distinction in the color densities of particular color patches between a processed control strip and the reference strip may indicate that the bath temperature for the processing of the final photographic print is not appropriate.

The common use of control strips as previously described herein with respect to photographic processing raises several issues. For example, it can be noted that the entirety of the processes described above involves some measurement of optical transmission densities (for the negative) and optical reflection densities (for the film paper). In addition, it is apparent that the measurement of the color densities of the reference strip and the control strips can involve a substantial amount of manual manipulation. Accordingly, it is clearly advantageous to employ a densitometer having the combined functions of reflection density measurement and transmission density measurement. In addition, it is also advantageous to provide a means for "automating" the density measurement functions, dependent upon the particular types of standardized reference and control strips being employed. For purposes of the description of the illustrative embodiment of the invention as subsequently disclosed herein, references to control strips will refer to both reference strips and control strips.

Another problem associated with the use of control strips is the requirement to essentially compare the color densities of patches on the control strips to expected color densities for the particular strips. That is, it is necessary to determine whether the color density "patterns" of the control strips fall within certain tolerances with regard to parameters such as patch size, predominant color, density and the like.

If only one type of control strip were to be utilized with a particular densitometer arrangement, this "pattern recognition" requirement would not present any substantial difficulties. That is, appropriate software for use with the central processing unit of the densitometer could be written for purposes of deriving the specific pattern recognition arrangement required for the specific control strip. However, if the densitometer is to utilize a variety of control strips, it would be somewhat difficult and complex to require the writing of different software packages for different strips. Further, certain control strips have multiple patterns. Accordingly, such patterns can actually be read erroneously in several different ways.

In addition, a substantial advance has been achieved in the art of densitometer development with an automated strip reader densitometer. This automated strip reader densitometer is disclosed in the commonly assigned U.S. Patent Application Ser. No. 309,342 filed Feb. 10, 1989 and referred to herein as the Cargill et al application. The disclosure of the Cargill et al application is hereby incorporated by reference herein. With the automated strip reader densitometer, control strips are essentially read "on the fly" as the control strips pass through various elements of the densitometer. With this type of arrangement, it is essentially necessary to provide a pattern recognition arrangement within the central processing unit which will have the capability of providing an indication as to a match or mismatch of the control strip with previously stored data as the control strip continuously moves through the densitometer.

SUMMARY OF THE INVENTION

In accordance with the invention, a system for measuring color characteristics of object samples under test includes memory means for storing color pattern data representative of desired color characteristic data. Reading means are provided for reading an object sample and generating data signals representative of measured color characteristic samples of the object sample. Processing means are connected to the reading means for processing the data signals and storing in the memory means measured data samples representative of the data signals. An improvement is provided wherein the processing means includes formatting means for formatting the measured data samples into a plurality of measured regions. Each of the measured regions represents a plurality of the measured data samples having common parameters within tolerances. Comparison means are provided for comparing the measured regions with the color pattern data. Indicating means generate signals indicative of whether one or more of the regions match or do not match the color pattern data.

The system also includes position determining means connected to the processing means for generating position signals indicative of positions of the measured color characteristic samples on the object sample. The processing means includes means for storing, as part of each of the measured data samples, position data indicative of the position signals. The system also includes motive means for automatically moving the object sample and/or the system relative to each other during reading of the object sample. The position signals comprise information indicative of the relative movement.

The color pattern data is stored in the memory means, so as to define individual color pattern regions. The comparison means compares the measured regions with the color pattern data by comparing the measured regions with the color pattern regions on a region-by-region basis.

The color pattern data for each of the color pattern regions comprises data representative of size, predominant color characteristics, color densities, transitions and relative position. The color pattern data for at least certain of the color pattern regions includes data defining whether a color pattern region is a SYNC region. The color pattern data for color pattern regions after the SYNC region comprises data representative of position relative to the SYNC region.

The color pattern data for each of the color pattern regions comprises, for an object sample requiring a plurality of passes through the system, data representative of a particular pass number, during which a color pattern region will be utilized for comparison. Also, the color pattern data for each of the color pattern regions comprises data defining region sizes and color density characteristics. In addition, data is provided which is representative of allowable deviations of the measured regions from the region sizes and color density characteristics.

The comparison means includes means for comparing sizes of the measured regions with sizes defined by the color pattern data. In addition, means are provided for comparing transitions of the measured regions with transitions defined for the color pattern data. Further, means are provided for comparing distances between the measured regions, with positional data defined for the color pattern data.

The comparison means also includes means for comparing predominant color characteristics of the measured regions, with predominant color characteristics defined for the color pattern data. In addition, the comparison means also comprises means for comparing color density characteristics of the measured regions, with the color density characteristics defined for the color pattern data.

The formatting means includes means for generating a set of measured region output data for each of the measured regions. The measured region output data includes data representative of transitions, size, position and color characteristics. The reading means includes means for reading the object sample in either of two opposing directions.

The object sample can include repeating color characteristic patterns. The color pattern data can be stored in the memory means so as to define an expected, repeating color pattern region. The processing means can include means for maintaining a count of the number of repeating color characteristic patterns found which match the repeating color pattern region.

The formatting means can include data sample comparison means for comparing color characteristics of successively obtained color samples. The data sample comparison means can include means for defining, for purposes of formatting measured regions, allowable tolerances of measured color characteristics of a data sample as a function of measured color characteristics of another data sample.

The reading means can include light source means for generating light rays and directing the light rays onto the object sample. Filter means are responsive to light rays from the object sample so as to discriminate predetermined color shade sets of spectral responses of the light rays from the sample. Detection means are responsive to light rays transmitted through the filter means for generating the data signals as representative of the intensities of light rays transmitted through the filter means.

Motive means can be connected to the processing means to automatically moving the object sample through the system adjacent the light source means. In this manner, an automated measurement of a plurality of color patches associated with the object sample can be made. Guide means can be mounted to the system and adjustable by an operator of the system. In this manner, guidance can be provided in at least one dimension of the object sample through the system.

The filter means can include reflection filter means positioned at a predetermined angle relative to the direction of object illumination by the light source means. The reflection filter means can be responsive to light rays reflected from the object sample, so as to discriminate a predetermined color shade set of spectral responses of the light rays. The filter means can also include transmission filter means positioned relative to the direction of object illumination by the light source means. The transmission filter means can be responsive to light rays transmitted through the object sample so as to discriminate a predetermined color shade set of spectral responses of the transmitted light rays.

The system can also include input means connected to the processing means, for providing operator input to the system. The indicating means can include display means connected to the processing means for providing visual display to an operator, indicative of function performed by the system.

A method in accordance with the invention can be adapted for use in a system for measuring color characteristics of object samples under test. The method can include storing of color pattern data representative of desired color characteristic data. An object sample can be read and data signals can be generated representative of measured color characteristic samples of the object sample. The method includes processing the data signals and storing, in the memory means, measured data samples representative of the data signals. In accordance to the invention, the method can further include the step of formatting the measured data samples into a plurality of measured regions, with each of the measured regions representing a plurality of the measured data samples having common parameters within tolerances. The measured regions can e compared with the color pattern data, and signals can be generated which are indicative of whether one or more of the measured regions match or do not match the color pattern data.

The method also includes generating position signals indicative of positions of the measured color characteristic samples on the object sample. As part of each of the measured data samples, position data can be stored indicative of the position signals.

The method can also include the step of automatically moving the object sample relative to the system during reading of the object sample. Position signals can be generated in accordance with the relative movement.

The storage of the color pattern data can include storage so as to define individual color pattern regions. The comparison of the measured regions with the color pattern data can include comparison of the measured regions with color pattern regions on a region-by-region basis.

The method can also include the step of defining a SYNC region for the color pattern regions. In addition, data representative of a particular pass number during which a color pattern region will be utilized for comparison can be defined, for at least certain of the color pattern regions. The method can also include comparison of sizes, transitions, relative positions, predominate color characteristics and color density characteristics of the measured regions with comparable parameters defined for the color pattern data.

The method can further include maintaining a count of the number of repeating color characteristic patterns of the object sample which match a repeating color pattern region of the color pattern data. Still further, the method can include defining, for purposes of formatting measured regions, allowable tolerances of measured color characteristics of a data sample as a function of measured color characteristics of another data sample.

BRIEF DESCRIPTION OF THE DRAWINGS

The invention will now be described with respect to the drawings, in which.

DESCRIPTION OF THE PREFERRED EMBODIMENTS

Figure 5:
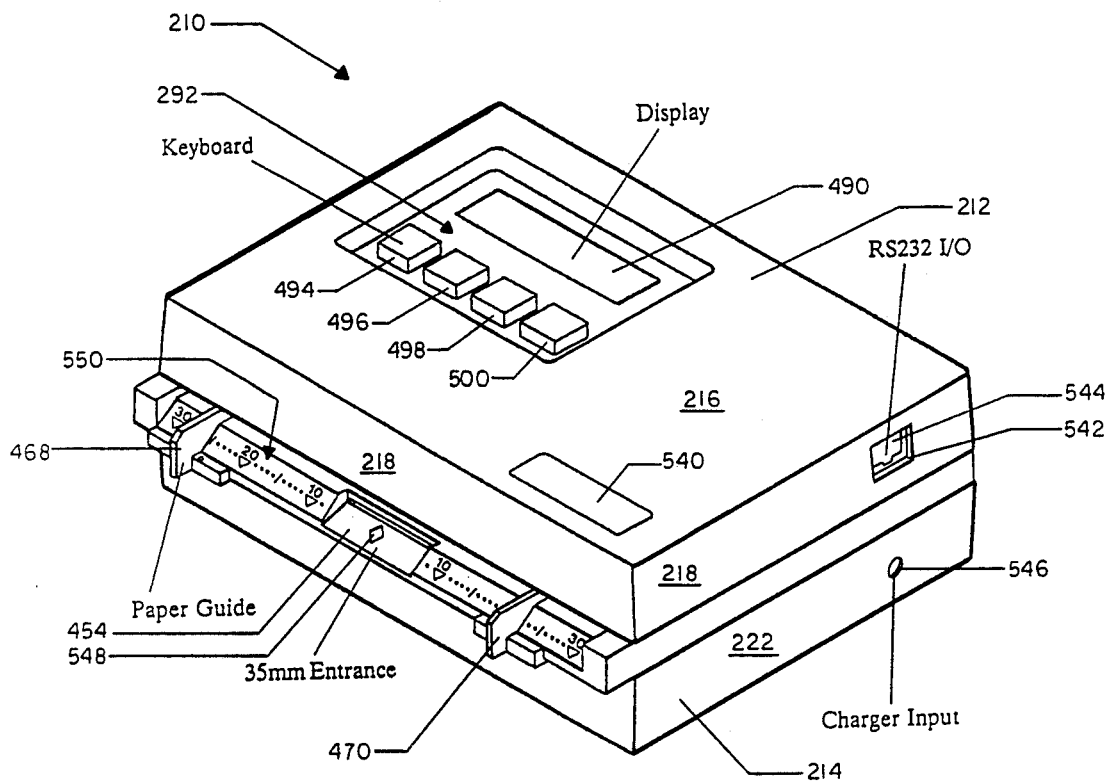
FIG. 5 is a perspective view of a densitometer apparatus which can be utilized in accordance with the invention.

The principles of the invention relate to apparatus and methods for pattern recognition and are disclosed, by way of example, in a densitometer apparatus 210 as illustrated in FIG. 5. The densitometer apparatus 210 comprises an automated strip reader color photographic densitometer, whereby film control strips, paper control strips and printer balance strips can be inserted for motorized and automatic measurements. In particular, the densitometer apparatus 210 is adapted to measure a plurality of different types of manufacturers' control strips, and sort data for measured fields, such as high density, low density and "stain." In addition, the densitometer apparatus 210 is adapted to display the data and, if desired by the operator, transmit the data to a peripheral device, such as a printer. A detailed description of the mechanical and electrical elements of the densitometer apparatus 210 are set forth in the disclosure of the commonly assigned and currently pending U.S. Pat. Application Ser. No. 480,331, filed Feb. 13, 1990, which is a continuation of commonly assigned U.S. Patent Application Ser. No. 309,342, filed Feb. 10, 1989, and now abandoned. The '331 patent application is hereby incorporated by reference herein.

As disclosed in the '331 Application, the densitometer apparatus 210 can provide an output of red, blue and green color density values for each measured field of a control strip. However, it will be apparent to those skilled in the appropriate arts that various other color density outputs could be achieved without departing from the principal concepts of the invention disclosed and claimed in the Cargill et al application. As also disclosed in the Cargill et al application, the densitometer apparatus 210 is adapted to measure both optical transmission densities (for film negatives) and optical reflection densities (for photographic paper) of the control strips. In addition, the densitometer apparatus 210 is also adapted to provide color density measurements of data aligned adjacent edges of a control strip or, alternatively, at the center of a control strip. Still further, the densitometer apparatus 21 is further adapted to provide automatic calibration for transmission and reflection densitometry.

The physical structure of the densitometer apparatus 210 is simply illustrated in FIG. 5. As previously described, details of the densitometer apparatus 210 are set forth in the Cargill et al application. Referring specifically to FIG. 5, the apparatus 210 comprises a relative compact structure suitable for use on a desk top or similar work surface. The apparatus 210 includes a top cover 212 and a bottom cover 214. The top cover 212 comprises an upper surface 216 having a rectangular configuration and integral with downwardly extending side surfaces 218 at the edges thereof. The bottom cover 214 comprises a lower and rectangular flat surface having outwardly extending side surfaces 222 integral with the flat surface.

Figure 7:
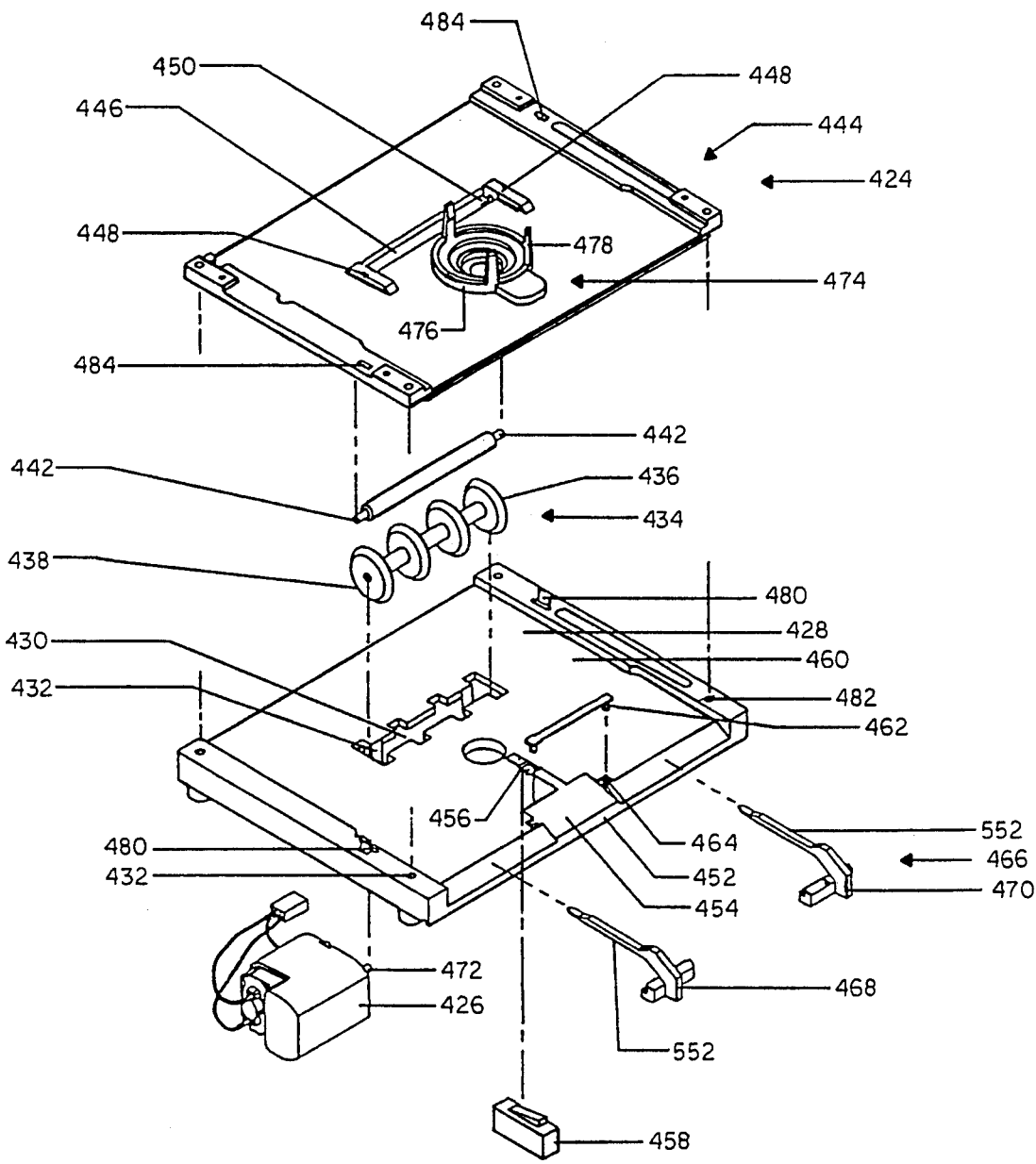
FIG. 7 is an exploded view of the densitometer apparatus shown in FIG. 6, and further showing the drive assembly for the apparatus.
Figure 8:
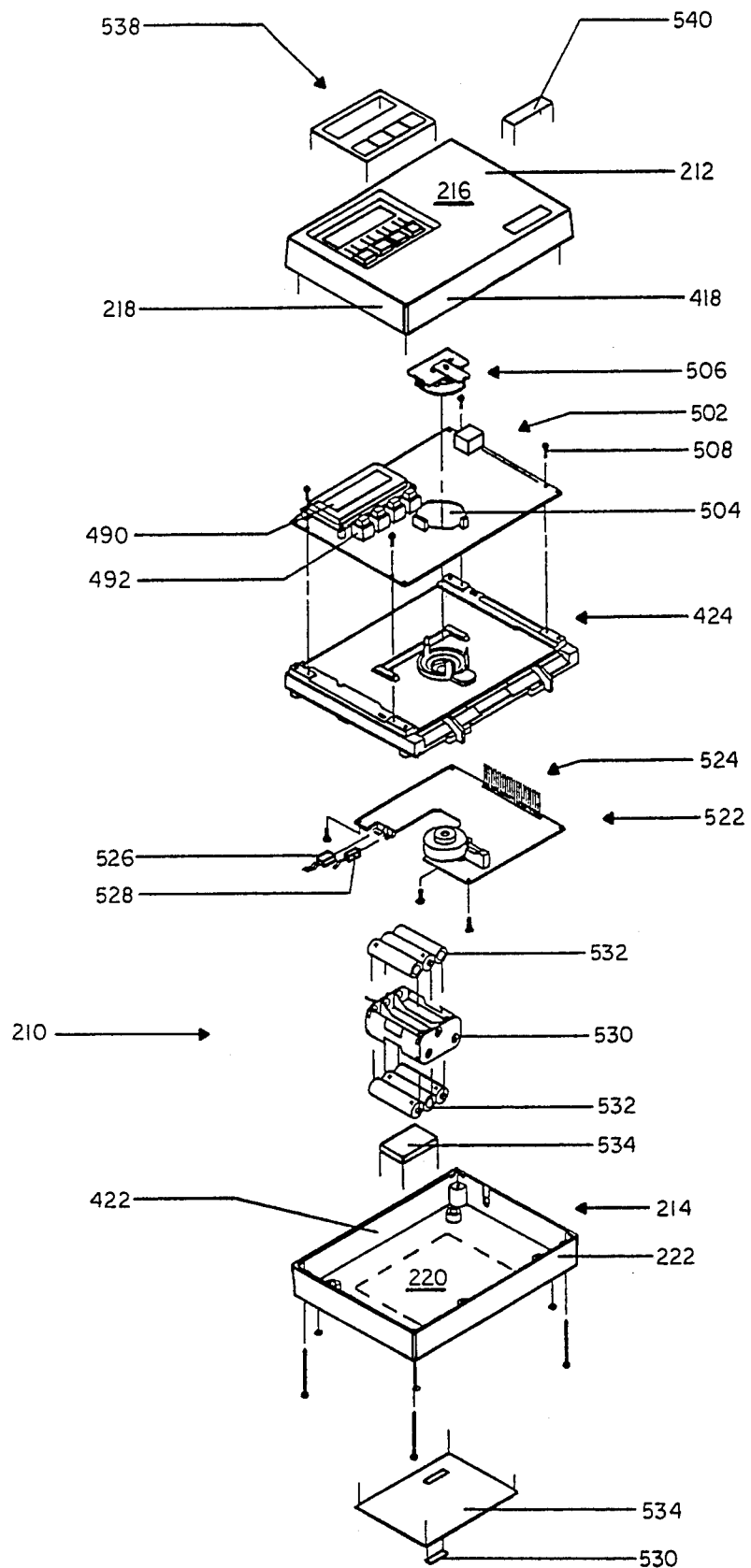
FIG. 8 is an exploded view of the apparatus shown in FIG. 5, and further showing various individual components of the apparatus.
Figure 9:
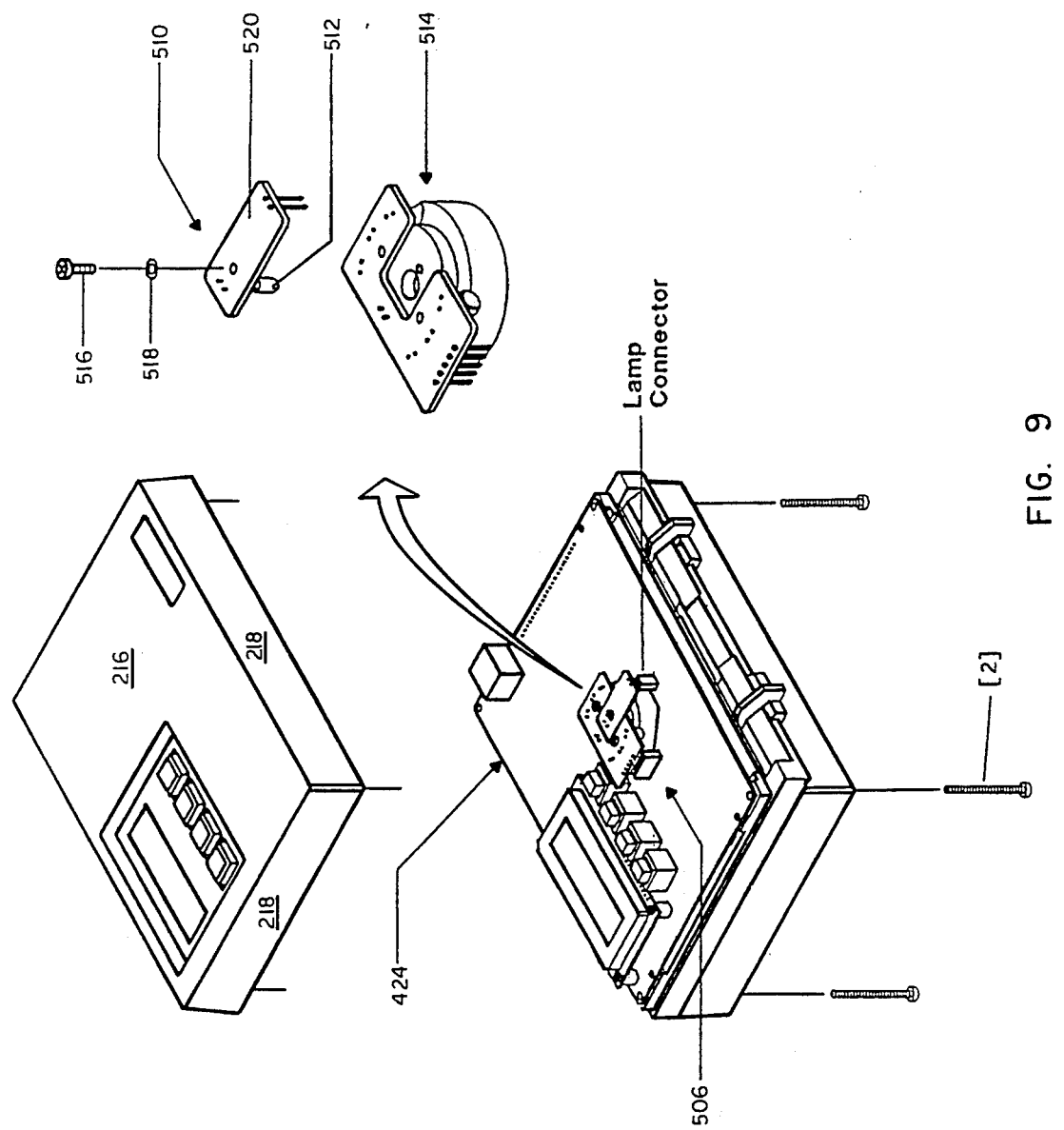
FIG. 9 is an exploded view of the apparatus shown in FIG. 5, and specifically showing elements of the lamp assembly of the apparatus.

Intermediate the top cover 212 and the bottom cover 214, and enclosed therebetween is a housing assembly 424 as primarily illustrated in FIGS. 7, 8 and 9, and specifically illustrated in an exploded view in FIG. 7. Referring specifically to FIG. 7, the housing assembly 424 comprises a motor assembly 426. The motor assembly 426 can be any of a series of conventional DC motors available on the commercial market. The housing assembly 426 further comprises a bottom housing 428 having a structural configuration as illustrated in FIG. 7. The bottom housing 428 includes an aperture 430 having slots 432 for purposes of receiving a drive wheel assembly 434 comprising an axle 436 with a series of drive wheels 438 axially positioned on the axle 436. The slots 432 are adapted to partially receive each of the drive wheels 438.

In addition to the drive wheel assembly 434, the housing assembly 424 also comprises an idler wheel assembly 440 comprising an elongated and cylindrical structure as further illustrated in FIG. 7. Attached to each end of the idler wheel assembly 440 are a pair of spindles 442. The housing assembly 424 further comprises a top housing 444 having a structural configuration as illustrated in FIG. 7. The top housing 444 includes an aperture 446 having an elongated configuration and through which the idler wheel assembly 440 is partially received. Located at each end of the elongated structure 446 is a brace 448 having recessed portions 450 adapted to rotatably receive the spindles 442 of the idler wheel assembly 440. Further, the braces 448 are spring loaded in a suitable manner so as to properly retain the idler wheel assembly 440.

Returning to the bottom housing 428 as illustrated in FIG. 7, the bottom housing further comprises a forward edge 452 having a slanted configuration and comprising a slightly recessed portion 454. The recessed portion 454 comprises a width appropriate for insertion of 35mm film strips for color density measurements utilized in the apparatus 210. The bottom housing 428 additionally includes a slot 456 adapted to receive a conventional microswitch assembly 458. The microswitch assembly 458 can comprise a "read" switch which is enabled by movement of a control strip into the densitometer apparatus 210 so as to activate the motor assembly 426.

The bottom housing 428 also comprises a film guide bar 460 having an elongated configuration and further having nubs 462 or similar elements adapted to be secured into slots 464 located adjacent the forward edge 452 of the bottom housing 428. In addition to the foregoing elements, a pair of film guides 466 are also included with the housing assembly 424. Specifically, the film guides 466 comprise a "left" film guide 468 and a "right" film guide 470. The film guides provide a means for guiding the control strip into the densitometer apparatus 210. Although not specifically shown in FIG. 7, the forward edge 452 of the bottom housing 428 can also comprise a series of numbered indicia indicating the relative positioning of the film guides 466.

As further shown in FIG. 7, the motor assembly 426 can comprise a driven shaft 472 which is adapted to be received through one end of the axle 436 of the drive wheel assembly 434. Accordingly, when the motor assembly 426 is activated, the drive shaft 472 will cause the drive wheel assembly 436 to rotate.

The top housing 444 can further comprise an optics assembly holder 474 which includes an aperture 476 which provides a slot for purposes of obtaining the transmission and reflection density measurements. The assembly holder 474 further comprises an annular portion 476 having a series of upright standards 478 extending upwardly therefrom.

For purposes of interconnecting the top housing 444 with the bottom housing 428, a pair of standards 480 are located substantially diagonal from each other and on opposing ledges 482 extending along opposing edges of the bottom housing 428. Correspondingly, the top housing 444 includes a pair of slots 484 positioned so as to be aligned with the standards 480. The alignment between the standards 480 and the slots 484 is such that the top housing 44 is essentially "snap" fitted with the bottom housing 428.

Returning to FIGS. 5 through 9, the densitometer apparatus 210 further comprises a visual display device 490 which can comprise a conventional LCD display device. In addition, the apparatus 210 also includes a keyboard 492 having a series of four key switches 494, 496, 498 and 500. The key switches on the keyboard 492 are conventional switches for providing manual input entry for the densitometer apparatus 210.

As illustrated in FIG. 8, the actual visual display device 490 and keyboard 492 are positioned on an upper printed circuit board assembly 502. The upper board assembly 502 includes an aperture 504 through which an optics assembly 506 can be mounted and secured to the previously described optics assembly holder 474 located on the housing assembly 424. As further illustrated in FIG. 8, the upper board assembly 502 can be simply mounted to the housing assembly 424 by means of screws 508 or other suitable connecting means.

As illustrated in FIG. 9, the optics assembly 506 can comprise a lamp assembly 510 adapted to secure and hold a suitable and conventional light source lamp 512. The lamp assembly 510 is secured within a lamp housing 514 by means of a conventional screw 516 and washer assembly 518. The components comprising the lamp assembly 510 and lamp housing 514 are relatively conventional in design with respect to known densitometer apparatus. The lamp assembly 510 can include a lamp printed circuit board 520 on which appropriate circuitry associated with the light source lamp 512 can be located.

As further illustrated in FIG. 8, the densitometer apparatus 210 can comprise a lower optics assembly 522 which can be characterized as a lower board assembly. The lower board assembly 522 can comprise circuitry associated with transmission density measurements by the apparatus 210. As further shown in FIG. 8, the lower board assembly can comprise a series of pins 524 comprising conventional elements for interconnecting the circuitry of the PC board assembly 522 to other circuitry associated with the apparatus. In addition, the lower board assembly 522 can include a pin connector 526 specifically adapted for providing circuit connections with the motor assembly 426. In addition, the board assembly 522 can also comprise an additional pin connector 528 suitable for connecting the circuitry of the board assembly 522 to power from batteries or the like.

As still further shown in FIG. 8, the apparatus 210 can comprise a battery holder assembly 530 adapted to receive a series of rechargeable batteries 532. The batteries 532 can provide a means for operation of the apparatus 210 without requiring any type of utility or external power. However, it should be emphasized that such a battery arrangement is purely optional.

For purposes of providing installation and appropriate positioning of the battery holder assembly 530, the apparatus 510 can further comprise a battery pad 534 positioned below the lower set of the batteries 532. In addition, if desired, the apparatus 210 can also include a back label 535 and serial number label 536. In addition, located on top cover 212, and positioned to be received over the display 490 and keyboard 494 can be a nameplate 538. Finally, a label 540 or other suitable identification means can further be positioned on the top cover 212.

Returning again to FIG. 6, the top cover 212 further comprises, in one side surface 218, an aperture 542 with an electrical receptacle 544 located within but spaced slightly apart from the aperture 542. The receptacle 544 comprises an input/output (I/O) port for a conventional RS 232 interface for purposes of providing a means for inputting data to and outputting data from the densitometer apparatus 410.

Figure 6:
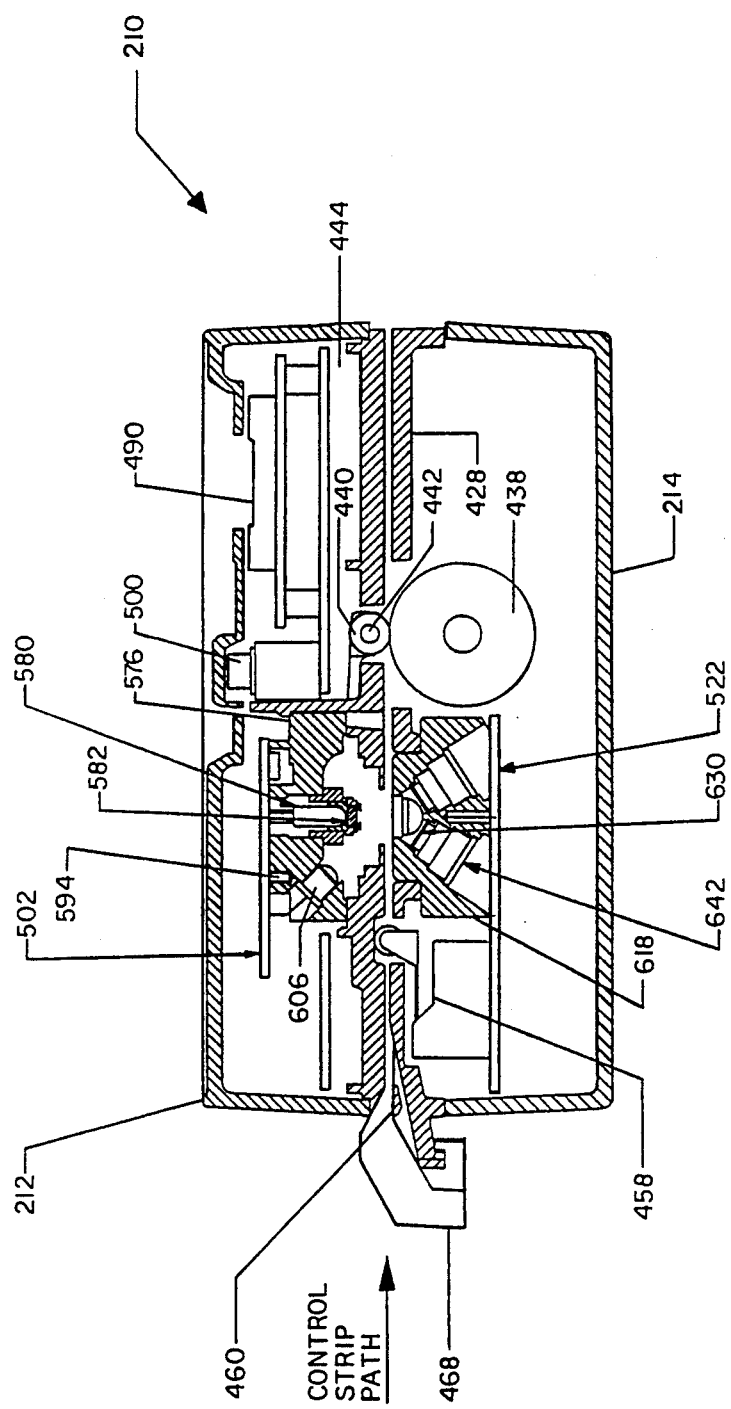
FIG. 6 is a cross-sectional diagram of a densitometer apparatus which may be utilized with the invention, illustrating the structural configuration of various elements of the apparatus.

In addition to the aperture 542, the densitometer apparatus 210 also comprises a second aperture 546 positioned on a side surface 222 of the bottom cover 214. Positioned within the aperture 546, but not specifically shown in FIG. 6, is an input receptacle for purposes of providing charger input for the batteries 532. Preferably, if the densitometer apparatus 410 comprises the batteries 532, the batteries 532 are conventional rechargeable batteries. The aperture 546, in combination with appropriate and conventional circuitry, can comprise a means for recharging the batteries 532 as necessary.

As further illustrated in FIG. 5, the recessed portion 454 of the housing assembly 424 can include a "diamond" or other appropriate indicia 548 for purposes of indicating the center of the path for color density measurements of the control strips. In addition, and as previously referenced the forward edge 452 of the bottom housing 428 of the housing assembly 424 can include numerical indicia 550 centered with respect to the diamond indicia 548 and extending lengthwise across the forward edge 452. The numerical indicia 550 provide a means for indicating appropriate settings of the left and right film guides 468 and 470, respectively.

As further shown in FIG. 5, the left and right film guides 468, 470 are conventional guides which are located at the forward edge 452 of the bottom housing 428 of housing 424. As shown in FIG. 7, the guides 468, 470 include elongated portions 552 which extend inwardly above the bottom housing 428 of housing assembly 424 and below the top housing 444. Each of the film guides 468, 470 is manually adjustable by the operator and comprise a means for guiding and controlling guidance of a control strip into the densitometer apparatus 410. FIG. 6 is a cross sectional view illustrating the configuration of the structural and circuit elements of densitometer apparatus 410 described herein.

Figure 10:
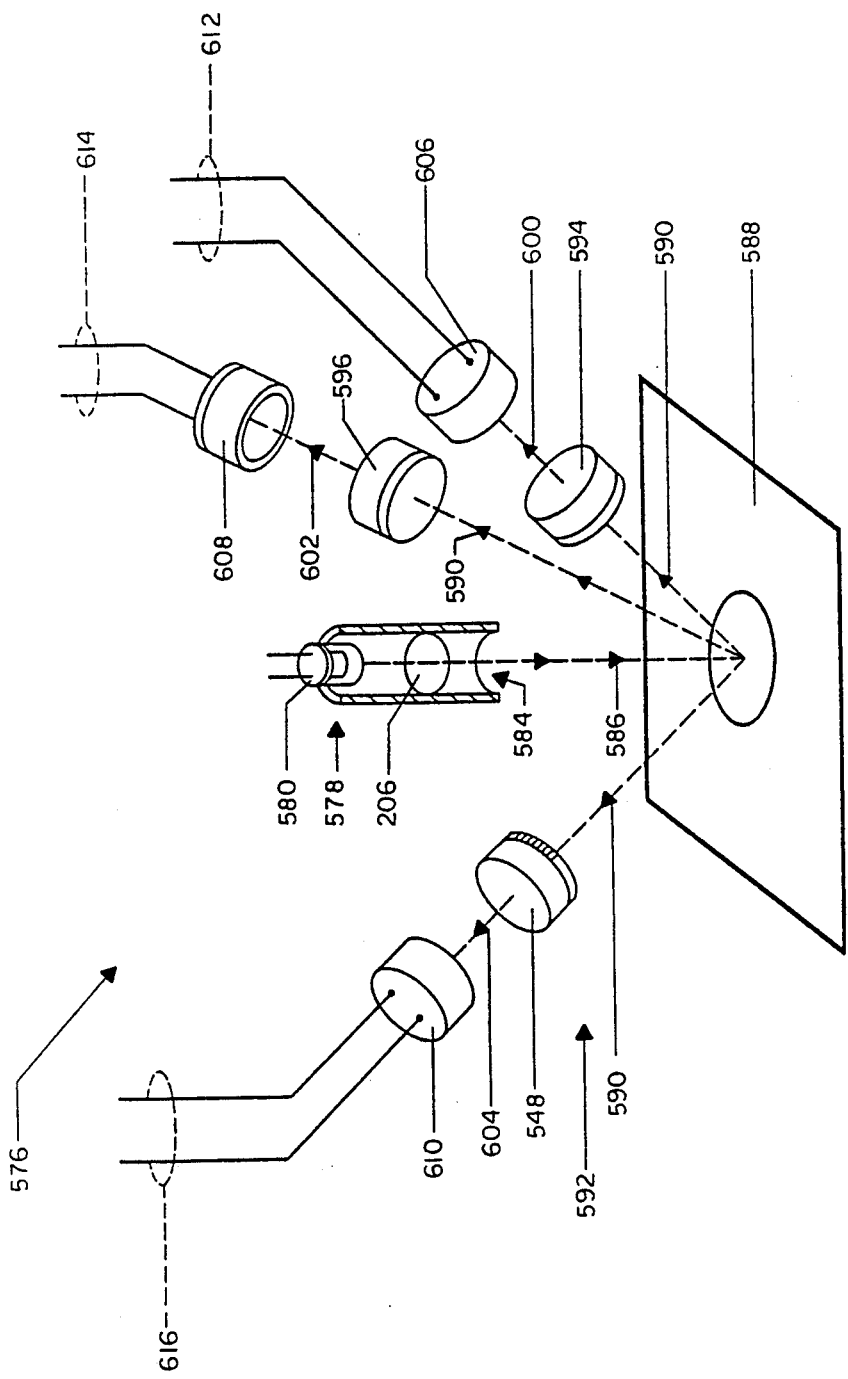
FIG. 10 is an illustration of the reflection optics assembly of the densitometer apparatus shown in FIG. 5.

Certain circuitry associated with the densitometer apparatus 210 will now be described with respect to FIGS. 10, 11 and 12. The densitometer apparatus 210 can include appropriate optics assemblies for measuring both transmission densities and reflection densities. FIG. 10 illustrates an exemplary reflection optics assembly 576 which can be utilized with the densitometer apparatus 210. Referring specifically to FIG. 10, and the numerical references therein, the densitometer apparatus 210 includes a light source unit or a lamp assembly 578 having a source light 580. Various standards have been developed for densitometer light source illuminants for optical density measurements in the field of photography. For example, densitometer standards have previously been described in terms of a tungsten lamp providing an influx from a lamp operating at a Planckian distribution of 3000K. Other suggested standards have been developed by ANSI and the International Organization for Standardization ("ISO"). These source light densitometry standards are typically defined in terms of the spectral energy distribution of the illuminant. The source light 580 preferably conforms to an appropriate standard and can, for example, comprise a filament bulb meeting a standard conventionally known in the industry as 2856K ANSI. As previously described, power for the source light 580 and other elements of the densitometer apparatus 410 can be provided by means of conventional rechargeable batteries or, alternatively, interconnection to AC utility power.

The source light 580 projects light through a collimating lens 582 which serves to focus the electromagnetic radiation from the source light 580 into a narrow collimated beam of light rays. Various types of conventional and well-known collimating lenses can be employed. The light rays transmitted through the collimating lens 582 project through an aperture 584. The dimensions of the aperture 584 will determine the size of the irradiated area of the control strip. Various standards have been defined for preferable sizes of the irradiated area. Ideally, the aperture 584 is of a size such that the irradiance is uniform over the entire irradiated area. However, in any physically realizable densitometer arrangement, such uniform irradiance cannot be achieved. Current standards suggest that the size of the irradiated area should be such that irradiance measured at any point within the area is at least 90% of the maximum value. In addition, however, aperture size is typically limited to the size of color bar areas to be measured, and is also sized so as to reduce stray light.

The light rays emerging from the aperture 584 (illustrated as rays 586 in FIG. 10) are projected onto the irradiated area surface of the control strip 588 under test. The control strip 588 may be a print balance strip or, alternatively, photographic paper or the like.

As the light rays 586 are projected onto the control strip 588, electromagnetic radiation shown as light rays 590 will be reflected from the control strip 588. As previously described in the section entitled "Background of the Invention", it is necessary to obtain quantitative measurements of this reflected light for purposes of determining the relative proportions of the light reflected from various object samples. As also previously described, it is substantially impossible to measure all of the light reflected from the control strip 588. Accordingly, standard detection configurations have been developed, whereby reflected light is detected at a specific angle relative to the illumination light rays 586 projected normal to the plane of the control strip 588. More specifically, standards have been developed for detection of reflected light rays at an angle of 45° to the normal direction of the light rays 586. This angle of 45° has become a standard for reflectance measurement and is considered desirable in that this configuration will tend to maximize the density range of the measurements. In addition, however, the 45° differential also represents somewhat of a relatively normal viewing configuration of a human observer (i.e. illumination at a 45° angle from the viewer's line of sight).

For purposes of providing light detection, a spectral filter apparatus 592 is provided. The filter apparatus 592 can include a series of filters 594, 596 and 598. The filters 594, 596 and 598 are employed for purposes of discriminating the cyan, magenta and yellow spectral responses, respectively. That is, each of the filters will tend to absorb light energy at frequencies outside of the bandwidth representative of the particular color hue of the filter. For example, the cyan filter 594 will tend to absorb all light rays, except for those within the spectral bandwidth corresponding to a red hue. By detecting reflected light rays only within a particular color hue bandwidth, and obtaining an optical density measurement with respect to the same, a "figure of merit" can be obtained with respect to the quality and color measurement of the control strip patch associated with that particular color hue.

Figure 1:
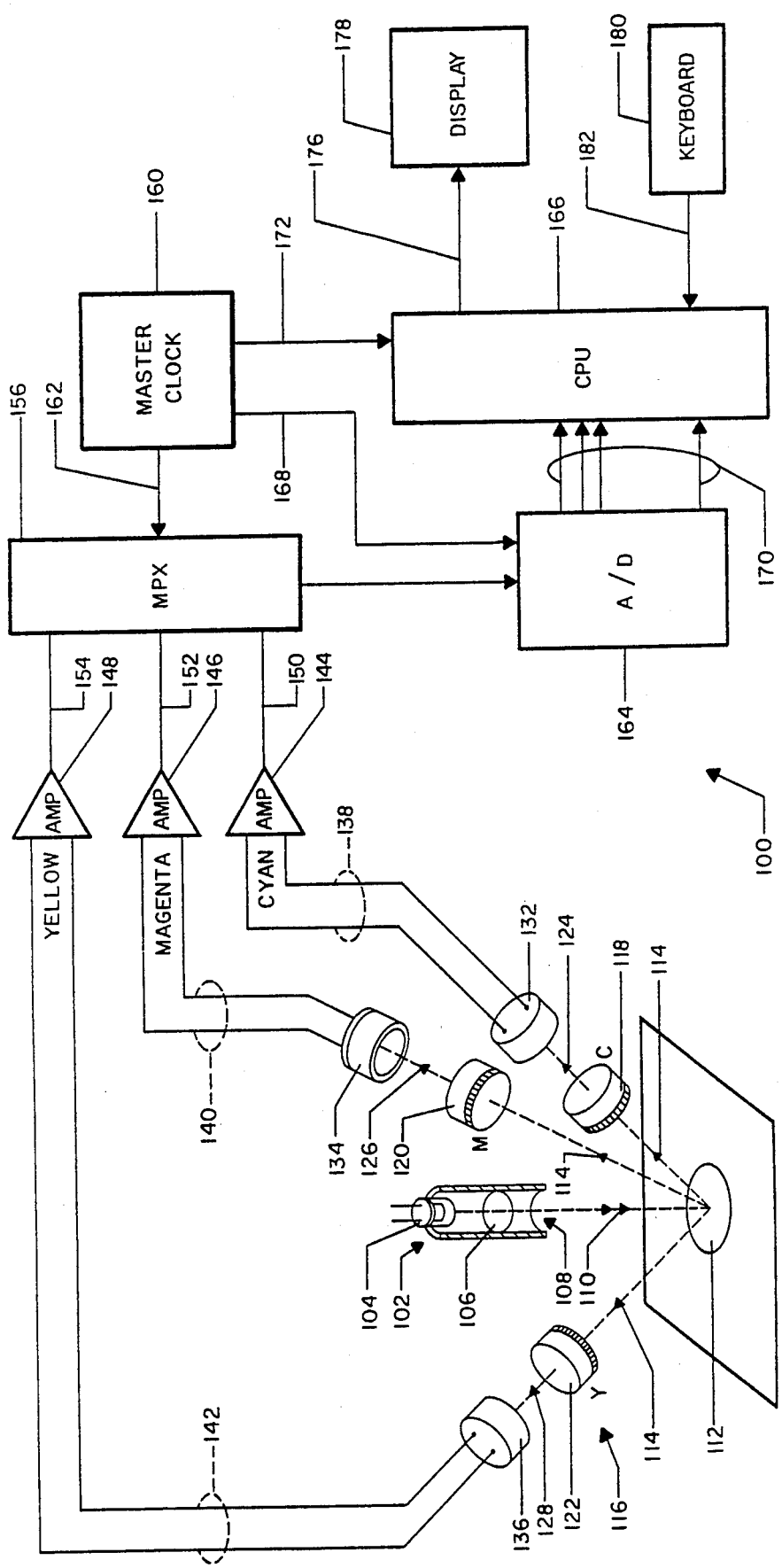
FIG. 1 is an illustrative embodiment of a prior art densitometer.
Figure 2:
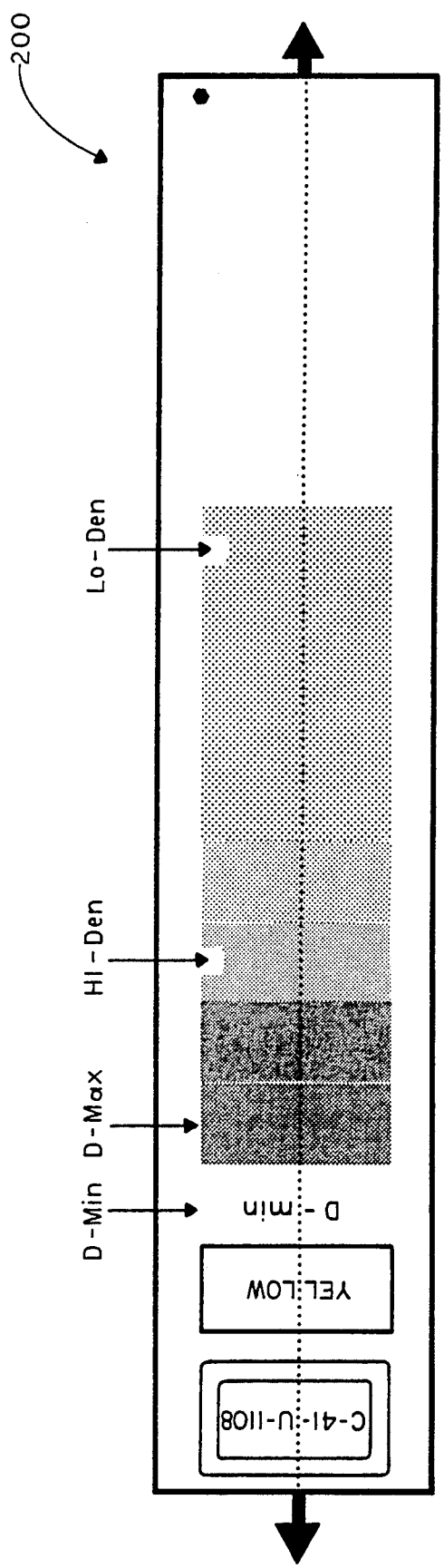
FIG. 2 is an illustrative embodiment of a control strip which can be utilized in accordance with the invention.
Figure 3:
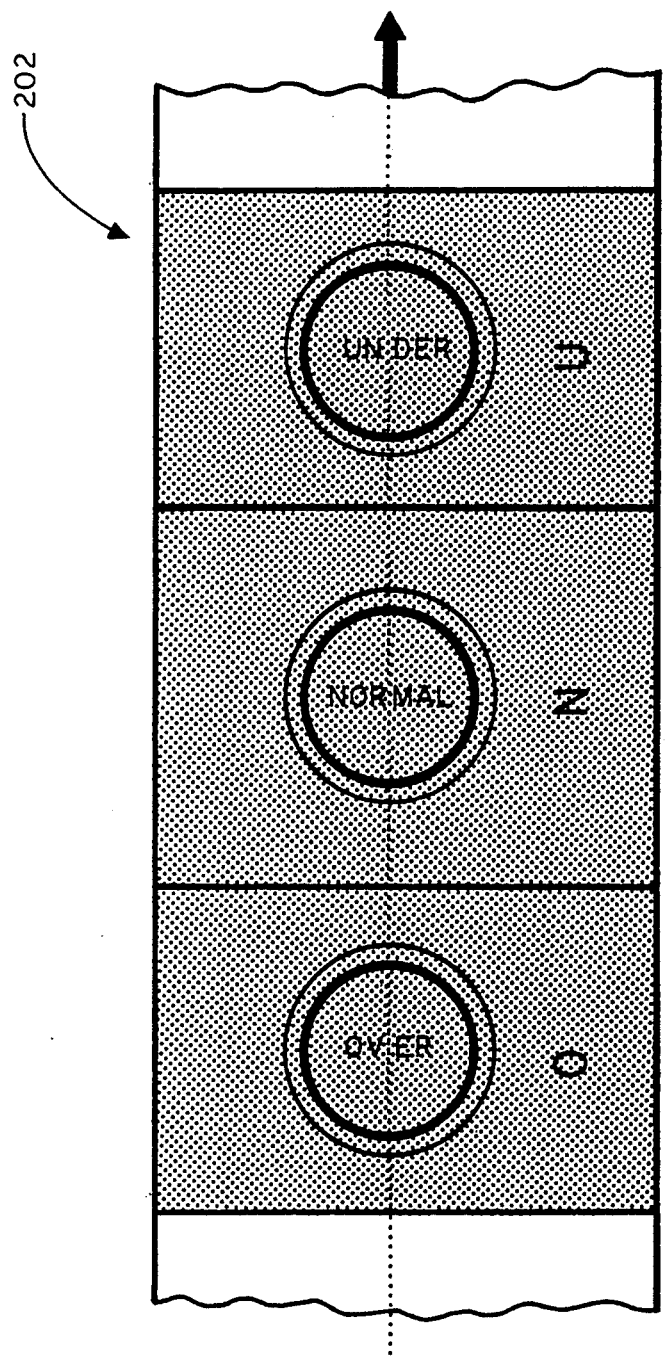
FIG. 3 is an illustrative embodiment of a print balance control strip which can be utilized in accordance with the invention.
Figure 4:
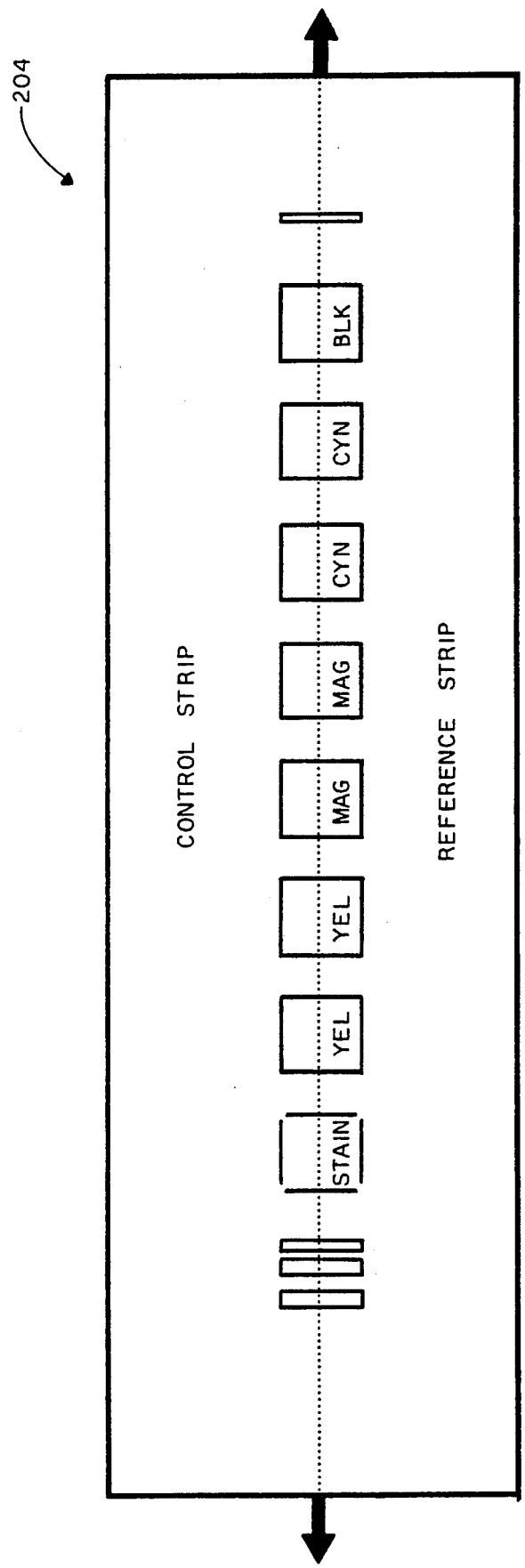
FIG. 4 is an illustrative embodiment of a further control strip which can be utilized in accordance with the invention.

It is apparent from the foregoing that the actual quantitative measurement of color density for reflectance is dependent in substantial part on the spectral transmittance characteristics of the filters. Accordingly, various well known standards have been developed with respect to spectral characteristics of densitometer filters. Standards were previously described with respect to the prior art densitometer apparatus 100 illustrated in FIG. 1. For example, Status A filters can be employed.

Although the filters 594, 596 and 598 are illustrated in the embodiment shown in FIG. 10 as the cyan, magenta and yellow color shades, other color shades can clearly be employed. These particular shades are considered somewhat preferable in view of their relative permanence and because they comprise the preferred shades for use in reflection densitometer calibration. However, it is apparent that different shades of red, blue and green, as well as entirely different colors, can be utilized with the densitometer apparatus 210.

The spectral filters 594, 596 and 598 may not only comprise various shades of color, but can also be of any several specific types of spectral response filters. For example, the filters can comprise a series of conventional Wratten gelatin filters and infrared glass. However, various other types of filter arrangements can also be employed.

As further shown in FIG. 10, the portion of the reflected light rays 590 which pass through the filters 594, 596 and 598 (shown as light rays 600, 602 and 604, respectively) impinge on receptor surfaces of photovoltaic sensor cells. The sensor cells are illustrated in FIG. 10 as sensors 606, 608 and 610 associated with the spectral filters 600, 602 and 604, respectively. The sensors 606, 608 and 610 can comprise conventional photoelectric elements adapted to detect the light rays eminating through the corresponding spectral filters. The sensors are further adapted to generate electrical currents having magnitudes proportional to the intensities of the sensed light rays. As illustrated in FIG. 10, the electrical current generated by the cyan sensor 606 in response to the detection of light rays projecting through the filter 608 is generated on line pair 612. Correspondingly, the electrical current generated by the magenta sensor 608 is applied to the line pair 614, while the electrical current generated by the yellow sensor 610 is applied as output current on line pair 616. Photoelectric elements suitable for use as sensors 606, 608 and 610 are well known in the art, and various types of commercially available sensors can be employed.

The magnitude of the electrical current on each of the respective line pairs will be proportional to the intensity of the reflected light rays which are transmitted through the corresponding spectral filter. These light rays will have a spectral distribution corresponding in part to the product of the spectral reflectance curve of the control strip sample 588 under test, and the spectral response curve of the corresponding filter. Accordingly, for a particular color shade represented by the spectral response curve of the filter, the magnitude of the electrical current represents a quantitative measurement of the proportion of reflectance of the control strip sample 588 within the frequency spectrum of the color shade.

Figure 11:
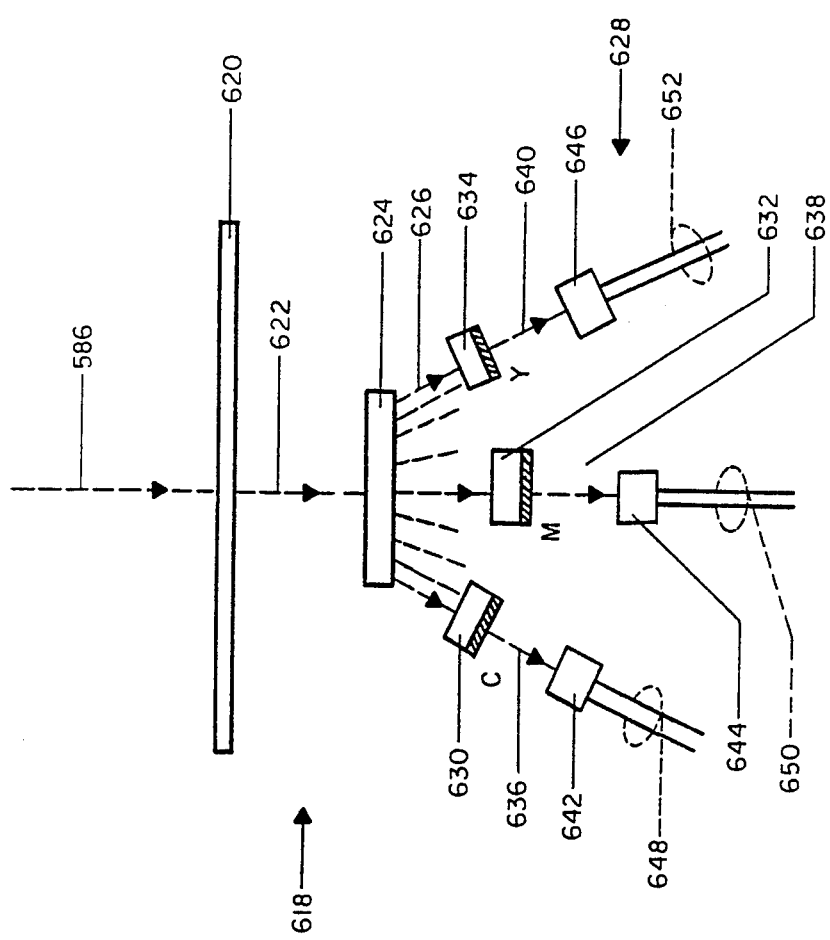
FIG. 11 is a partially schematic diagram of the transmission optics assembly of the densitometer apparatus shown in FIG. 5.

The densitometer apparatus 210 can include not only a reflection optics assembly 576 as previously described with respect to FIG. 10, but can further include a transmission optics assembly 618 depicted in simplified schematic form in FIG. 11. As previously described, the transmission optics assembly 618 is mounted on the lower board assembly 522. The exact method and structure associated with the mounting of the transmission optics assembly 618 will be apparent to one skilled in the art of optics and densitometer design, and will not be described in detail herein.

Referring specifically to FIG. 11, a film control strip 620 for which transmission density is to be measured is positioned so that the light rays 586 from the source light 580 (previously described with respect to FIG. 10) are projected from above the film control strip 620 onto the irradiated area surface of the strip 620. The film control strip 620 may be any of numerous types of materials for which the transmission density will provide an indication of the photographic quality of the associated photographic process. For example, the control strip 620 can be a film negative.

As the light rays 586 are projected onto the film control strip 620, electromagnetic radiation shown as light rays 622 will be transmitted through the control strip 620. For purposes of determining the relative proportions of the light transmitted through various object samples, it is necessary to obtain quantitative measurements of this transmitted light. However, it is substantially impossible to measure all of the light transmitted through the control strip 620. Accordingly, the transmitted light rays 622 are projected through a diffuser element 624 which causes the light rays to be substantially uniformly diffused. The diffuser element 624 is a relatively common and well known optical device, and can be characterized as an "opal." The diffused light rays transmitted through the diffuser element 624 are shown in FIG. 11 as light rays 626.

For purposes of providing light detection, a spectral filter apparatus 628 is provided. The filter apparatus 628, similar to the filter apparatus 592 described with respect to FIG. 12, comprises a series of three filters 630, 632 and 634. The filters 630, 632 and 634 are employed for purposes of discriminating the red, blue and green spectral responses (cyan, magenta and yellow), respectively. That is, each of the filters will tend to absorb light energy at frequencies outside of the bandwidth representative of the particular color hue of the filter. By detecting reflected light rays only within a particular color hue bandwidth, and obtaining an optical density measurement with respect to the same, a "figure of merit" can be obtained with respect to the quality of the object sample coloring associated with that particular color hue.

The spectral filters 630, 632 and 634 can be positioned at any of a number of desired angles relative to the plane of the opal 624 and the control strip 620. Although FIG. 11 shows the filters of the filter apparatus 628 in a two dimensional elevation view, the filters of the apparatus 628 will actually be angled in a manner similar to the configuration shown in the perspective view of FIG. 10 with respect to the reflection filters. Further, although the filters 630, 632 and 634 are illustrated in the embodiment shown in FIG. 11 as the red, blue and green color shades, other color shades can clearly be employed.

It is apparent from the foregoing that the actual quantitative measurement of color density of transmittance is dependent in substantial part on the spectral transmittance characteristics of the filters. Accordingly, various well-known standards have been developed with respect to spectral characteristics of transmittance densitometer filters. For example, these filters can be filters commonly characterized as Status M filters.

Like the reflection filters previously described, the filters of the filter apparatus 628 are maintained stationary and utilized to simultaneously receive the light rays 626 transmitted through the control strip 620. Accordingly, it is unnecessary for the user to manually rotate or otherwise sequentially move spectral transmittance filters into receptive positions.

As further shown in FIG. 11, the portion of the transmitted light rays 626 which pass through the filters 630, 632 and 634 (shown as light rays 636, 638 and 640, respectively) impinge on receptor surfaces of photovoltaic sensor cells. The sensor cells are illustrated in FIG. 11 as sensors 642, 644 and 646 associated with the spectral filters 630, 632 and 634, respectively. The sensors 642, 644 and 646 can comprise conventional photoelectric elements adapted to detect the light rays eminating through the corresponding spectral filters. The sensors are further adapted to generate electrical currents having magnitudes proportional to the intensities of the sensed light rays. As illustrated in FIG. 11, the electrical current generated by the red sensor 642 in response to the detection of light rays projecting through the filter 630 is generated on line pair 648. Correspondingly, the electrical current generated by the blue sensor 644 is applied to the line pair 650, while the electrical current generated by the green sensor 646 is applied as output current on line 652. Photoelectric elements suitable for use as sensors 642, 644 and 646 are well known in the art, and various types of commercially available sensors can be employed.

The magnitude of the electrical current on each of the respective line pairs will be proportional to the intensity of the reflected light rays which are transmitted through the corresponding spectral filter. These light rays will have a spectral distribution corresponding in part to the product of the spectral transmittance curve of the control strip 620, and the spectral response curve of the corresponding filter. Accordingly, for a particular color shade represented by the spectral response curve of the filter, the magnitude of the electrical current represents a quantitative measurement of the proportion of transmittance of the control strip 620 within the frequency spectrum of the color shade.

Figure 12:
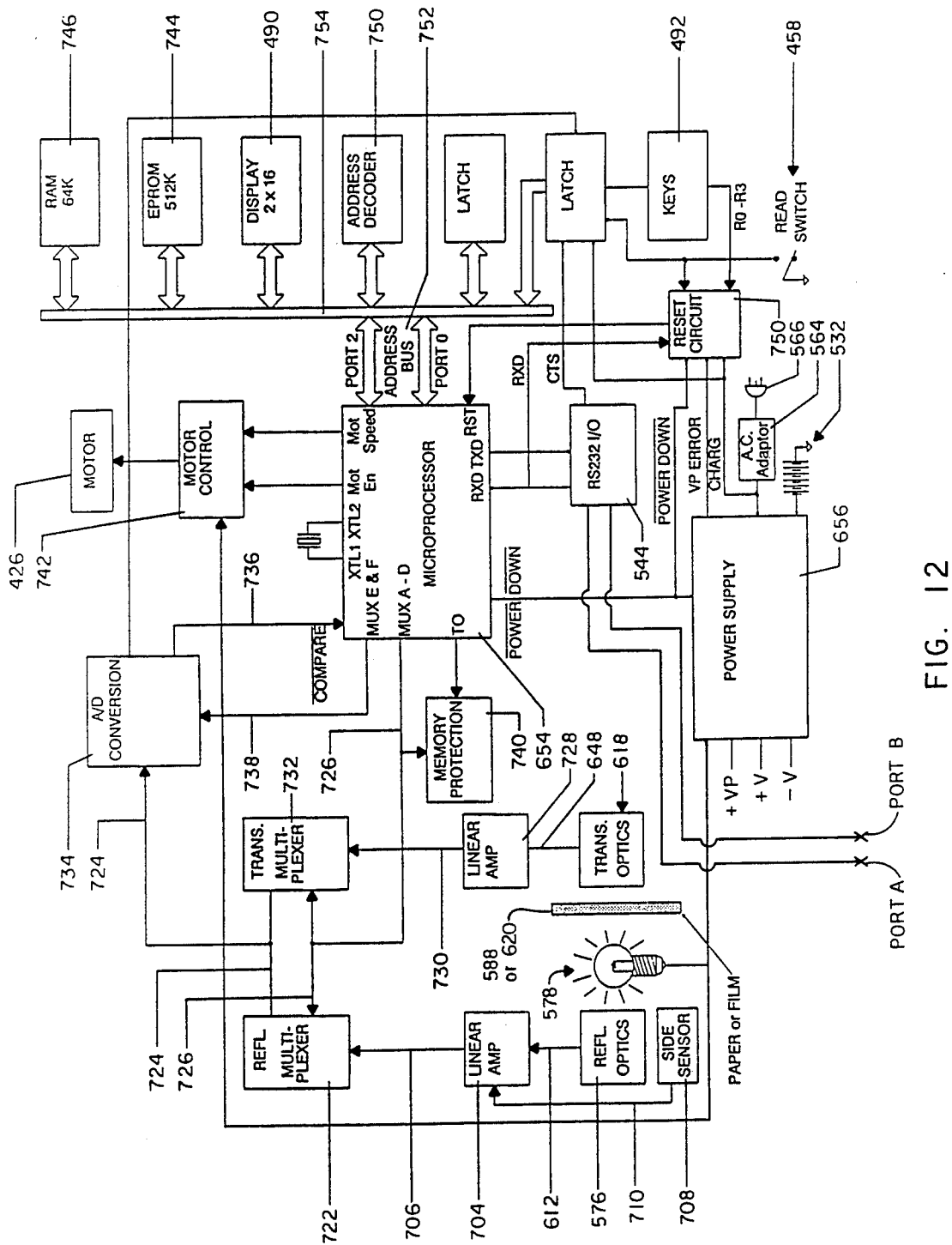
FIG. 12 is a partially schematic diagram of circuit elements of the densitometer apparatus shown in FIG. 5.

A general simplified block diagram of the electronics of the densitometer apparatus 210 is illustrated in FIG. 12. As shown therein, and as previously described, the densitometer apparatus 210 includes a light source unit 578 utilized for measuring color densities of the control strip 588 or 620. If the control strip is control strip 588, the apparatus 210 is adapted to measure reflection density. If the control strip is strip 620, the apparatus 210 is adapted to measure transmittance density through the use of the transmittance optics assembly 618. For purposes of description, although the reflection optics assembly 576 and the transmission optics assembly 618 each comprise three spectral filters and photosensors, and three paths for determining the color densities of different color hues of the spectrum, the electronics associated with the same will be described only with respect to one path. Accordingly, as shown in FIG. 12, only the line pair 612 is shown as being interconnected to the reflection optics assembly 576. Correspondingly, only the line pair 648 is shown as being interconnected with the transmission optics assembly 618. However, other line pairs as previously described with respect to FIGS. 10 and 11 will be interconnected to each of the optics assemblies 576 and 618.

As further shown in FIG. 12, the densitometer apparatus 210 includes a conventional microprocessor 654 utilized for purposes of obtaining data representative of color densities of a control strip under test, and further utilized to control various activities associated with operation of the apparatus 210. For these purposes, the microprocessor 654 will comprise various control programs adapted to perform a number of functions associated with operation of the apparatus 210. The relevant control programs will become apparent from the functions and the general operation of the densitometer apparatus 210 as described in subsequent paragraphs herein. Accordingly, the actual control programs will not be described in detail.

Returning to FIG. 12, the densitometer apparatus 210 includes a relatively conventional power supply 656. The power supply 656 is adapted to provide power to various elements of the circuitry of apparatus 410.

When the reflection optics assembly 576 is utilized, an electrical current representative of the reflectance is applied on line pair 612 as an input signal to the conventional linear amplifier 704. The amplifier 704 is responsive to the current output of the associated sensor on line pair 612 to provide a means for converting low level output current from the respective sensor on the corresponding line pair 612 to a voltage level signal on the conductor 706. The voltage level of the signal on the conductor 706 is of a magnitude suitable for subsequent analog-to-digital (A/D) conversion functions. Such amplifiers are well known in the circuit design art and are commercially available with an appropriate volts per ampere conversion ratio, bandwidth and output voltage range. The magnitude of the output voltage on conductor 706 represents the intensity of reflected light rays transmitted through the corresponding spectral filter.

The densitometer apparatus 210 also includes a side sensor 708 which is utilized to compensate for changes in lamp intensity of the source light 578. Output from the side sensor 708 is applied to the linear amplifier circuit 704 on transmission line 710.

Each of the voltage signal outputs from the linear amplifier circuitry for each color channel are applied as input signals to a single conventional multiplexer 722. For example, the output voltage from linear amplifier circuitry 704 is applied on the transmission line 706 as an input signal to the reflection multiplexer 722. It should be emphasized that although there are three linear amplifier circuits, one for each color channel, only a single reflection multiplexer 722 is provided. The multiplexer 722 operates so as to time multiplex the output signals from each of the linear amplifier circuits (including linear amplifier circuit 704) onto the conductive paths 724 and 726. Timing for operation of the reflection multiplexer 722 can be provided by means of clock signals from a conventional master clock. During an actual density measurement of a control strip, the densitometer apparatus 210 will utilize a segment of the resultant multiplexed signal which sequentially represents a voltage output signal from each of the linear amplifier circuits associated with different color channels.

Correspondingly, as further illustrated in FIG. 12, the current output signal on line pair 648 from the transmission optics assembly 618 is applied to a linear amplifier circuit 728. A linear amplifier circuit 728 is provided for each of the color channels associated with the transmission optics assembly 618. The linear amplifier circuit 728 provides a means for converting low level output current from the respective sensor on the corresponding line pair 648 to a voltage level signal on the conductor 730. The voltage level of the signal on the conductor 730 is of a magnitude suitable for subsequent A/D conversion functions.

As further shown in FIG. 12, the voltage signal output from the linear amplifier circuitry 728 on conductive path 730 is applied as an input signal to a conventional transmission multiplexer 732. Like the reflection multiplexer 722, the transmission multiplexer 732 operates so as to time multiplex the output signals from each of the linear amplifier circuits associated with the transmission optics assembly 618. Again, timing for operation of the multiplexer 732 can be provided by means of clock signals from a master clock. During an actual transmission density measurement of a control strip, the densitometer apparatus 410 will utilize a segment of the resultant multiplexed signal which sequentially represents a voltage output signal from each of the linear amplifier circuits associated with the transmission optics assembly 618.

The resultant multiplexed signal from the transmission multiplexer 732 is applied as an output signal on the conductive path 724. The resultant multiplexed signal from either the reflection multiplexer 722 or the transmission multiplexer 732 is applied as an input signal to a conventional A/D converter 734. The A/D converter 734 comprises a means for converting the analog multiplexed signal on the conductive path 724 to a digital signal for purposes of subsequent processing by the microprocessor 654. The A/D converter 734 is preferably controlled by means of clock pulses applied from a conventional master clock.

As illustrated in FIG. 12, the digital output signals from the A/D converter 734 are applied as input signals on transmission line 736 to the microprocessor 654. Further, the microprocessor 654 is utilized to provide various control signals to the reflection multiplexer 722 and transmission multiplexer 732 (on transmission line 726). Still further, control signals are also applied from the microprocessor 654 to the A/D converter 734 by means of the transmission line 738. In addition to the foregoing elements, the densitometer apparatus 210 also comprises a memory protection circuit 740 which is further controlled in part by the microprocessor 654. The memory protection circuit 740 is conventional in design and comprises a well known arrangement for protecting the memory against power surges and power outages.

As previously described, the densitometer apparatus 210 also comprises a motor 426. The motor is operated under control of a motor control circuit 742 as illustrated in FIG. 12. Correspondingly, the motor control circuit 742 is controlled by the microprocessor 654, with power being supplied by the power supply 656. Various types of motor control circuits can be employed with the densitometer apparatus 210.

The microprocessor 654 is utilized for control of various functions associated with the densitometer apparatus 410. Numerous types of conventional and commercially available microprocessors can be employed for the microprocessor unit 654. An exemplary microprocessor could, for example, comprise the Intel 80C31 8-Bit CMOS Microcomputer commercially available from the Intel Corporation.

The densitometer apparatus 210 also comprises an address decoder 750 interconnected to the address bus 752 of the microprocessor 654. The address decoder 750 is utilized to decode the address range for the various devices associated with the bus 754. The address decoder 750 is conventional in design.

As also previously described, the densitometer apparatus 210 includes an EPROM 744 which can comprise, for example, a CMOS 512K EPROM. In addition, the apparatus 410 can also comprise the random access memory 746. The RAM 746 can, for example, comprise an 8192 byte static random access memory.

As also previously described, the densitometer apparatus 210 can include a series of key switches 492. These key switches will operate in conjunction with a reset circuit 750 as illustrated in FIG. 12. As previously described, the reset circuit 750 is controlled in part by the microprocessor 654.

Greater detail with respect to the previously described elements of the densitometer apparatus 210, and the operation thereof with respect to uses of control strips are described in the previously referenced Cargill et al application. Briefly, when a particular control strip is to be "selected" by the operator, the microprocessor 654 is programmed so as to generate appropriate data to the display 490 which will identify various aspects of the control strip. In addition, the apparatus 210 can display various information on the display 490 relating to the guide setting positions for the guides 468 and 470.

The densitometer apparatus 210, in summary, is adapted to operate as an automated instrument for measuring color densities of film control strips, paper control strips and printer balance strips. The apparatus 210 is motorized and comprises fixed optics assemblies for purposes of measuring the color densities. As desired, the microprocessor 654 can be programmed so as to appropriately sort data for measuring various control strip fields. The adjustable guides accommodate differing sized control strips for use with the apparatus 210.

With respect to aspects of the invention, it is necessary to include prestored data comprising a library of preprogrammed strip formats (paper, film and printer balance). Data to be stored with respect to the strip formats includes identification data for the particular control strips, the sequence of color areas expected on the control strips and other appropriate relevant data.

When a control strip is to be read, the strip is inserted in the appropriate slot formed with the guides 468 and 470. If the control strip is a 35mm strip, it can be immediately inserted into the apparatus 210 in the slot 454.

In accordance with the invention, the densitometer apparatus 210 employs a pattern recognition arrangement for purposes of comparing data from a control strip "read" by the apparatus 210 to a pattern stored in the constant memory 744 of the apparatus 210. This pattern recognition sequence is utilized to compare the control strips read by the apparatus 210 with expected data from the control strips.

For purposes of determining whether a control strip "matches" a particular pattern, various criteria are utilized. For purposes of further description, the previously stored data relating to a particular pattern will be referred to as the "pattern definition." Correspondingly, data read by the densitometer apparatus 210 will be referred to as the "current" data or data relating to the "current" color patch of a control strip. In other cases, the pattern definition previously stored in memory will be referred to as the "selected" pattern.

With reference again to the criteria for purpose of pattern recognition, one criteria relates to the size of the color patch. That is, a determination is made as to whether the current color patch being evaluated by the densitometer apparatus 210 falls within predetermined tolerances associated with the pattern definition. Another criteria relates to the predominant "color" of the currently evaluated color patch. That is, a determination is made as to whether the predominant color of the current color patch falls within the scope of various tolerances associated with the expected color as determined by the pattern definition.

Still further, the pattern definition criteria can include a determination as to whether the color density values associated with the current color patch fall within expected tolerances as determined by the pattern definition. In addition to the color density, a determination must also be made as to whether the color patch edges are expected to be lighter or darker than the color patch itself. These patch edges are commonly referred to as "transitions" of the color patch. With respect to this criteria, a determination is made as to whether the area surrounding the current color patch is lighter or darker than the patch itself.

As described in greater detail herein, a determination in accordance with the invention is also made with respect to the "distance" between color patches associated with a particular control strip. As explained in greater detail, a determination is made as to whether the distance between two measured regions of a current control strip fall within tolerances defined by the selected pattern definition. With respect to the foregoing, the apparatus 210 can be adapted so as to provide a determination that a "match" has occurred with respect to a particular control strip, if all of the aforedescribed criteria associated with the control strip fall within the tolerances defined by the selected pattern definition.

In accordance with the invention, the pattern recognition functions can be performed by various software stored in memories and executed by use of the microprocessor 654. However, it should be emphasized that if absolutely necessary, it would be possible to perform the functions described herein by discrete hardware components, notwithstanding that such operation would be substantially inefficient. In the following description, it can be assumed that particular functions described with respect to pattern recognition are performed by various computer programs executed through use of the microprocessor 654. With the following description, the actual instruction sequences associated with the computer programs required for purposes of performance of the pattern recognition procedures will be apparent to those skilled in the appropriate arts.

In accordance with the invention, a pattern recognition procedure is performed substantially as a two-step process. As a control strip is read by the densitometer apparatus 210 as previously described herein, various data is obtained as the control strip passes through the apparatus 210. This data is stored in appropriate buffers as will be described in subsequent paragraphs herein.

In general, each data "sample" obtained by the densitometer apparatus 210 will be composed of three color samples (i.e., red, green and blue or other appropriate samples as desired) and a "distance" stamp. In accordance with the invention, distances can be determined by the actual "count" or rotations or partial rotations associated with use of the motor 426. That is, as the drive motor 426 moves the control strip through the densitometer 210, a "count" of pulses associated with the drive motor 426 can be accumulated. In this manner, relative distances can be determined by keeping track of a relative "position" of color measurement data as associated with particular pulses from the drive motor 426.

With respect to the pattern recognition procedure, the first step of the procedure can be referred to as a "presort" procedure. In this procedural step, a scan is made of the data accumulated during passage of the control strip through the densitometer 210. The particular data can then be formatted so as to essentially construct a series of "regions", which can be generally defined as a plurality of successive data samples having color samples which are "constant" within predetermined tolerances. The properties associated with each region can include not only density measurements for each color (i.e., red, green and blue), but also transitional data. As previously described, such transitional data can be utilized to determine whether the areas immediately "leading" and immediately "following" a current region are lighter or darker than the region itself. In addition to this data, the pulse count associated with the motor 426 can be utilized so as to define starting and ending coordinates of the particular region.

Following the presort procedure, whereby a series of "regions" are constructed for the current control strip, a second step is performed by comparing the data defined by this series of regions with the data associated with the selected pattern definition. In accordance with the invention, this comparison can be per formed on a region-by-region basis. Accordingly, the actual pattern definition previously stored within the memories of the densitometer apparatus 210 is also composed of data formatted as a series of regions, with each pattern region having various parameters and tolerances defined therein.

To further generally describe the pattern recognition procedure in accordance with the invention, the recognition procedure associated with this second pattern recognition step commences by characterizing the first pattern region in the definition as a "sync" region. In this manner, distance measurements associated with subsequently defined regions are characterized as being relative to the sync region. Thereafter, for purposes of comparing each region in the formatted region data associated with the current control strip, with the selected pattern regions, determinations are made as to whether density, transitional data and the like fall within the scope of predetermined tolerances. If a region is determined which matches the selected pattern region, this region is defined as a sync region and the starting and ending coordinates associated with the region are stored in appropriate memory for subsequent functions.

After a sync region has been determined, the subsequent pattern region is evaluated with respect to the previously described criteria. More specifically, the "distance" associated with the subsequent pattern region is either added to or subtracted from the location of the sync region. The result of this addition or subtraction thereafter becomes the "target" value for a subsequent region. Thereafter, the measured regions are again "scanned" to determine if a region entry has been made in which the target value is bounded by beginning and ending coordinates (again based on motor pulse counts).

If an appropriate entry is found in which a target value is bounded by the beginning and ending coordinates, and the region is determined to "match" the pattern region, the "color data" from the particular measured region can be extracted and stored in appropriate memory locations.

Thereafter, the next successive pattern region is evaluated and the aforedescribed process is repeated. That is, through the use of addition or subtraction of the distance field, a target value is determined. A determination is then made so as to look for a measured region having beginning and ending coordinates bounding the target value. If such a measured region is found, a determination is made as to whether the appropriate criteria match the pattern region. If so, color data associated with the measured region is obtained and appropriately stored.

The aforedescribed process is continuously repeated until all pattern regions have been evaluated and "used", or until one of the aforedescribed determinations fails. If a failure occurs, appropriate data and instruction sequences are reset and reinitiated, and a search for a sync region is resumed immediately following the physical location where the last sync region was determined. If the end of the measured data is found before a valid strip is recognized, the pattern recognition procedure in accordance with the invention can actually scan the data again, but this time in a reverse direction. This reversal of data scanning can be utilized to determine if the control strip was possibly inserted in the opposite direction.

The aforedescribed pattern recognition procedure in accordance with the invention can be utilized for most control strips. However, certain strips exist in which the areas to be measured do not necessarily have what can be characterized as "reliable" boundaries. In such a situation, an "absolute" measurement can be taken directly from the sampled data, bypassing actual regions which have been constructed by use of the presort step of the pattern recognition procedure.

In data and instruction sequences associated with the pattern definition, a flag or "absolute" switch can be set, indicating that the pattern recognition procedure should proceed based on absolute measurements. If this occurs, distance measurements provided within the pattern definition can be converted into motor pulse counts. The sampled data can then be scanned until a measurement is found that is greater than an expected motor pulse count. Color samples at that particular location can then be converted to densities and utilized as measured data.

In addition to the foregoing, a relatively "special" case exists for printer balance strips. With printer balance strips, in contrast to other types of control strips, a repeating single pattern (usually a bull's eye) exists. In other types of control strips, a relatively distinct pattern will be provided, such as in the case of paper or film strips.

As previously described with respect to the background of the invention and the structure of the densitometer apparatus 210, a relatively common form of a printer balance strip is a UNO sequence, referring to the "under", "normal", and "over" sequence. In such printer balance strips, three prints will exist of a single pattern, with one printed from an underexposed negative, one printed with a properly exposed negative, and one printed from an overexposed negative. Further, printer balance strips can also exist as a single-print format, five-print format, and an "n"-print format, where "n" can be anything from 1 to 35 prints. In addition, all of these formats can actually be printed in various sizes, can be cropped to save paper, and can also be printed either vertically or horizontally.

With these types of printer balance strips, the normal procedure for utilizing the size of the region and the distance between regions as recognition criteria is inappropriate. Accordingly, and in accordance with the invention, such printer balance strips are treated as a repeating pattern, in which the pattern definition defines the parameters for one region, and that definition is expressly used repeatedly for all regions on the control strip. Accordingly, after the presort has constructed the data into the region formats, the aforedescribed pattern recognition procedure can commence a search for a sync patch or region as previously disclosed. However, in contrast to the previously described procedure, when a pattern is determined which essentially "fits" the entirety of the pattern definition, the procedure is not considered complete. Instead, the search is continued through the data so as to determine additional "valid" patterns. In addition, a "count" is maintained of the number of patterns found. When the end of the data for the control strip is reached, the count is compared to an expected count which may be previously stored or, for eXample, entered by the operator through the keys 492 previously described with respect to FIG. 12. A comparison is then made between the actual count and the entered expected count. If the counts are determined to match, the control strip is considered to be a valid control strip. Correspondingly, if the counts do not match, an appropriate message indicative of an invalid reading can be generated by the apparatus 210 and applied to the display 490. This message can further provide information to the operator that the control strip should again be read through the densitometer apparatus 210.

The operation and greater detail associated with the pattern recognition procedure will now be described in the subsequent paragraphs herein. As previously described, the first step of the pattern recognition procedure (referred to as the "presort" step) comprises the scanning of an entire array of accumulated data from the passage of a control strip through the densitometer apparatus 210. As also previously described, this data is then formatted into a series of "regions" in which the color measurements do not vary by more than predetermined amounts, as subsequently described herein.

Figure 16:
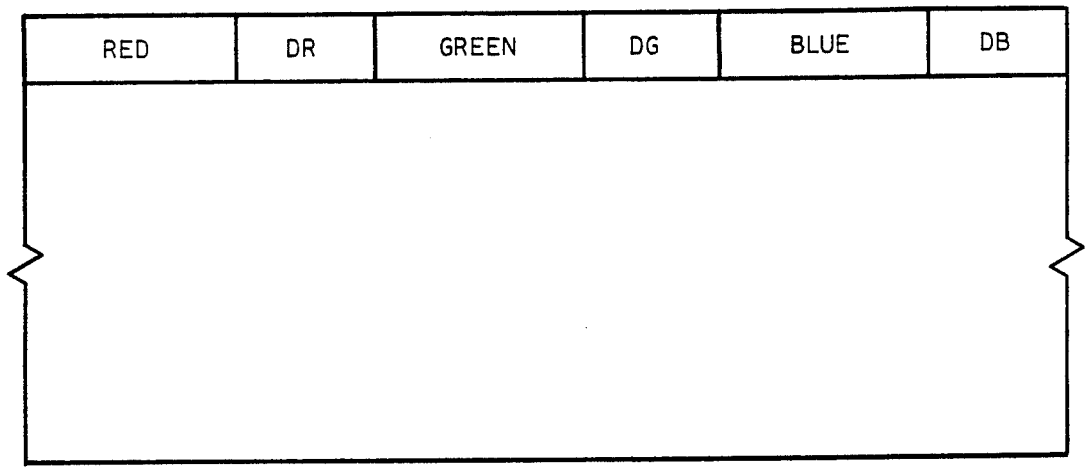
FIG. 16 illustrates an exemplary embodiment of a configuration which may be utilized for entry of raw data associated with the pattern recognition procedure in accordance with the invention.

For this presort procedure, FIG. 16 illustrates an exemplary embodiment of an input data format which may be utilized with respect to the data obtained as the control strip is passed through the apparatus 210. FIG. 16 specifically illustrates a single entry of "raw" data obtained by the apparatus 210. In the particular embodiment illustrated in FIG. 16, each single entry of raw data comprises 15 bytes. The 3-byte variable identified as the "red" variable comprises a 24-bit reflectance or density measurement for the red channel. Correspondingly, the "green" 3-byte variable and "blue" 3-byte variable each comprise 24-bit reflectance or density measurements for the green and blue channels respectively. In addition to this data, the variable identified as the "Dr" variable comprises a 2-byte variable indicating the distance measurement associated with the red reflectance or density value. The "Dg" and "Db" variables identify the distance measurements associated with the green and blue reflectance values, respectively. As previously described, and in accordance with the invention, the distance measurements can be characterized in terms of motor revolutions or the like.

Figure 17:
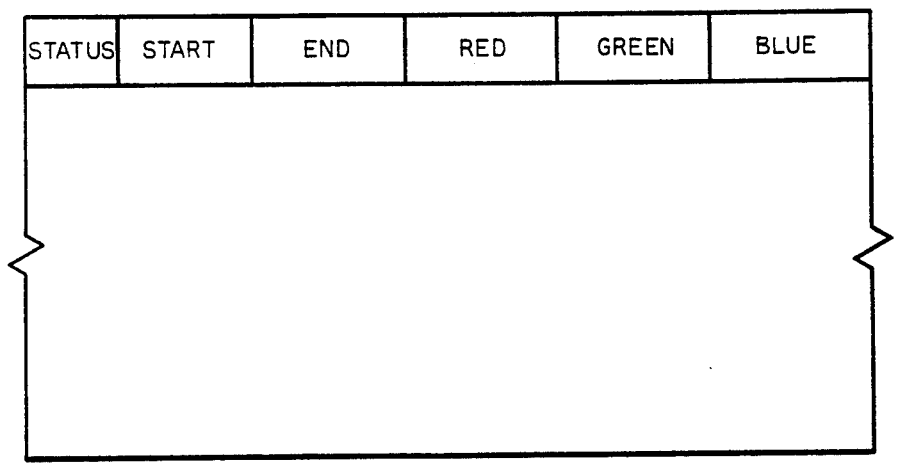
FIG. 17 illustrates an exemplary embodiment of a format for output data associated with the pattern recognition procedure in accordance with the invention.

With respect to the formatting of the raw data into regions, FIG. 17 illustrates an exemplary embodiment of a single region entry which may be utilized as an output data format for the region formatting. As shown in FIG. 17, each single entry can comprise, for example, 11 bytes of data. The status variable can comprise one byte with information indicating beginning and ending transitions. For example, 1 bit could be utilized for indicating a beginning transition, with a value of "1" indicating the transition is from darker to lighter, while a bit value of "0" would indicate a transition from lighter to darker. A corresponding bit of the status variable could also be utilized to indicate the ending transition. In addition, a particular bit configuration within the status variable can also indicate an "end of data".

The start variable can comprise, for example, two bytes, and indicate an absolute distance measurement from the beginning of the control strip, for the beginning of the particular region indicated by this entry. The end variable can comprise, for example, two bytes indicating the absolute distance measurement from the beginning of the strip for the end of this particular region. Correspondingly, each of the red, green and blue variables can comprise, for example, two bytes and contain the density measurements taken as an averaged value for each of the colors red, green and blue. In this instance, it is preferable that a minimum number of samples is required for each color, in order to consider a particular area as a valid region.

For purposes of actually determining if two consecutive samples of a given color are considered to "match", the following equation can be utilized:

$$R1 = R2 +/- (R1/12 + C) \qquad \text{(Equation 2)}$$

where R1 is equal to the reading for the first color sample, R2 is equal to the reading for the second color sample and C is a constant dependent upon whether the readings relate to a reflection or transmission reading. If R1 is within the bounds provided by the right-hand side of Equation 2, then the two color samples being compared can be considered to be "matching". It will be apparent to those skilled in the pertinent arts that various other types of "matching" formulas can be utilized without departing from the spirit and scope of the novel concepts of the invention.

Figure 14:
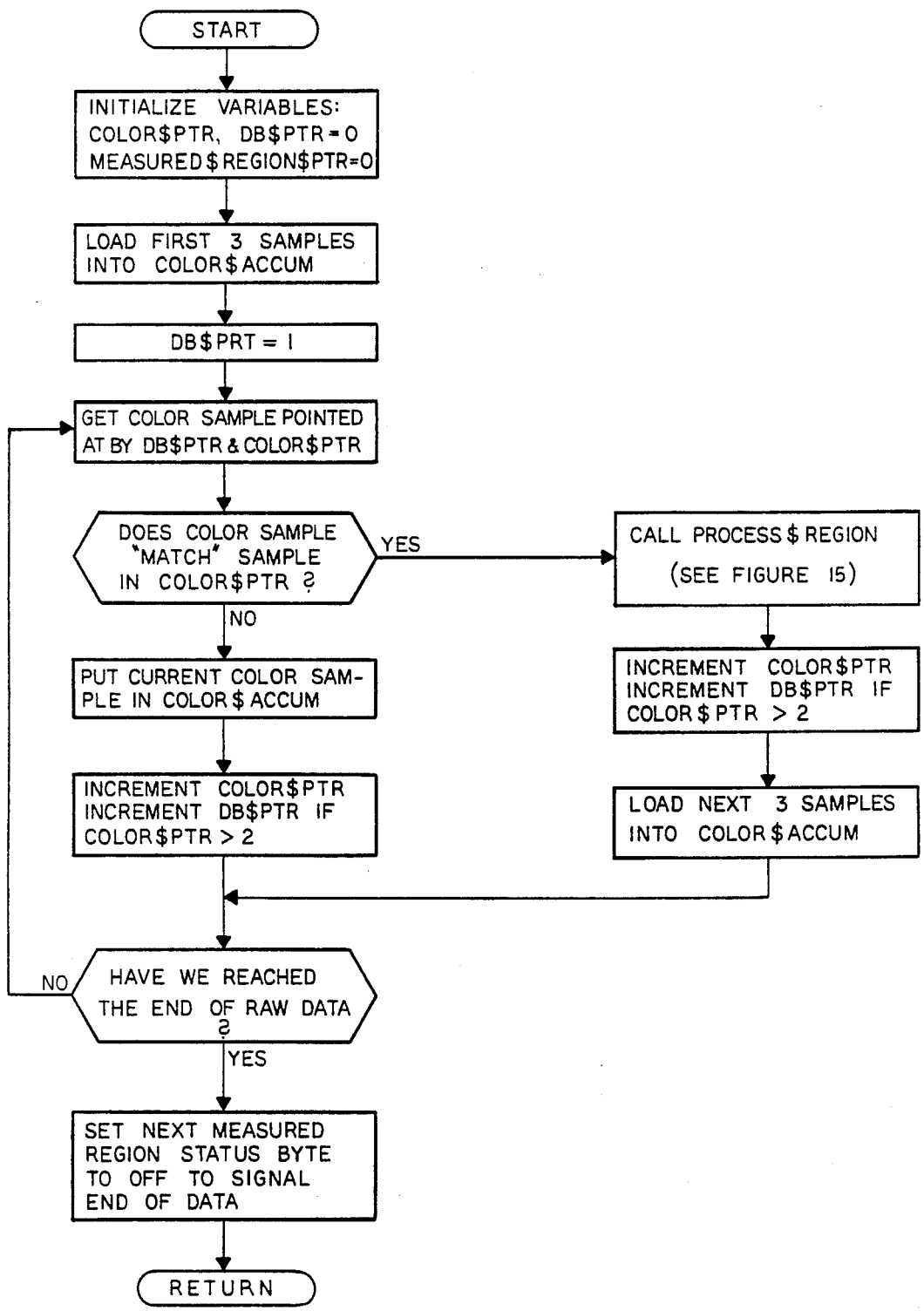
FIG. 14 is a sequence diagram showing certain sequences associated with the presort step of the pattern recognition procedure in accordance with the invention.
Figure 15:
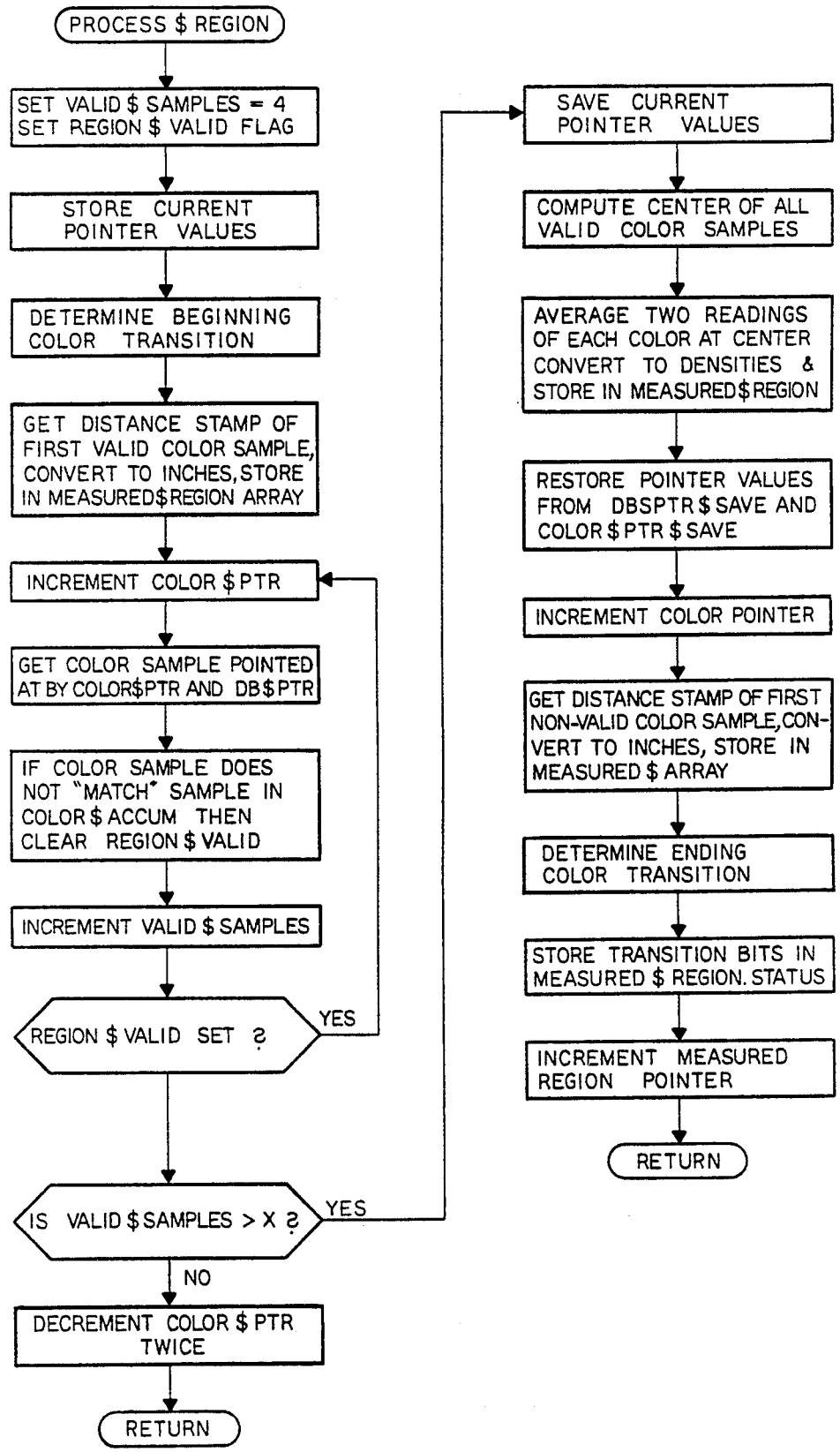
FIG. 15 is a further sequence diagram showing other aspects of the processing of regions associated with the presort sequence.

An operational sequence diagram of the presort procedure is provided in FIGS. 14 and 15. As shown in FIG. 14, the presort sequence diagram commences by initializing certain variables, including the variable color$ptr which identifies a color pointer which essentially "points" at a single color in the element which is "pointed" to by the variable db$ptr. In the particular embodiment described herein, this variable can have only three values; namely 0 (representing red), 1 (representing green), and 2 (representing blue). The variable db$ptr represents a "data base" pointer comprising the index into the raw data array. Each element of this array is composed of red, green and blue reflectances or densities and a distance stamp for each color as previously described herein with respect to FIG. 16.

A further variable identified in the sequence diagrams of FIGS. 14 and 15 is referred to as the color$accum. This variable is identified as the color accumulator and comprises a plurality of bytes for each of the red, green and blue colors. Correspondingly, the variable identified as measured$region$ptr essentially "points" to the currently defined region. As shown in FIG. 14, certain of these variables are initialized and the first three samples are stored in the color accumulator. The data base pointer is then set to 1, and the color sample which is pointed to by the data base pointer and the color pointer is then retrieved.

A determination is then made as to whether the color sample "matches" the sample in the color accumulator. If the sample matches, sequence control is passed to the sequence diagram identified as process$region in FIG. 15. As described in subsequent paragraphs herein, this function will continue to compare color samples and increment pointers until a failure of a color comparison may occur. A measured region is constructed and control is then returned to the presort sequence.

If the color sample does not match the sample in the color accumulator, the then current color sample is stored in the color accumulator. The color pointer is then incremented, along with the data base pointer.

A determination is then made as to whether the end of the raw data has been obtained. If the end of the raw data has not been achieved, an additional color sample is obtained as determined by the data base pointer and the color pointer. Correspondingly, if the end of the raw data has been obtained, the "next measured region" status byte is set to an appropriate value so as to signal the end of the raw data. A return is then made to normal sequence control.

Referring again to the situation where the color sample matches the sample in the color accumulator, after the process$region sequence functions have been executed, a return is made to the presort sequence. The color pointer is then incremented, along with the data base pointer. The next three color samples are then stored in the color accumulator, and control is returned to the functions associated with a determination as to whether the end of the raw data has been obtained.

Referring specifically to FIG. 15, and the sequence diagram identified as the process$region sequence diagram, a variable identified as the valid$samples variable is specifically set to 4, and the region$valid flag is also set. Current pointer values are then stored, and a determination is made as to the beginning of the color transition With respect to this determination, a comparison is made between the last non-matching color sample and the sample of the same color immediately following.

Thereafter, the distance stamp is obtained for the first valid color sample, converted to appropriate distance parameters, and stored in the measured$region array. The color pointer is then incremented, along with the data base pointer.

With further reference to FIG. 15, the color sample which is pointed to by the color pointer and the data base pointer is then obtained. If this color sample does not match the sample in the color accumulator, the variable identified as the region$valid is cleared.

Following this function, the variable identified as the valid$samples is incremented, and a determination is made as to whether the region$valid variable is set. If this variable is set, a return is made to the function associated with the increment of the color pointer.

If the region$valid variable is not set, the valid$samples variable contains the number of actual valid color samples. A determination is then made as to whether the valid$color samples are greater than a predetermined number, required for purposes of determining a valid region. If not, the color pointer variable is decremented and a return is made to the sequence described in FIG. 14.

If the valid$samples variable is of a sufficient value, the current pointer values are saved, and stored in appropriate memory locations. A computation is then made of the "center" of all of the valid color samples, or a similar computation is made for determining a value for the "color" of the region. In the particular embodiment shown in FIG. 15, the computation of the center is made by averaging two readings of each color at the center, with the appropriate data stored in the measured$region variable.

A restoration is then made of pointer values from the variables associated with the data base pointer and the color pointer. An increment is then made of the color pointer, and a distance stamp is obtained of the first non-valid color sample, which is stored in the measured$region array.

A determination is then made of the ending color transition, and the appropriate transition data is stored in the measured$region status variable. An increment is then made of the measured region pointer, and a return is made to the presort sequence illustrated in FIG. 14.

As previously described herein, following the presort pattern recognition procedure, a "recognition procedure" is provided. In this procedure, a comparison is made between the region data generated by the presort procedure and the predefined pattern definition which is also stored in a region format. An extraction is made of the proper color density data if the comparison is successful.

Figure 18:
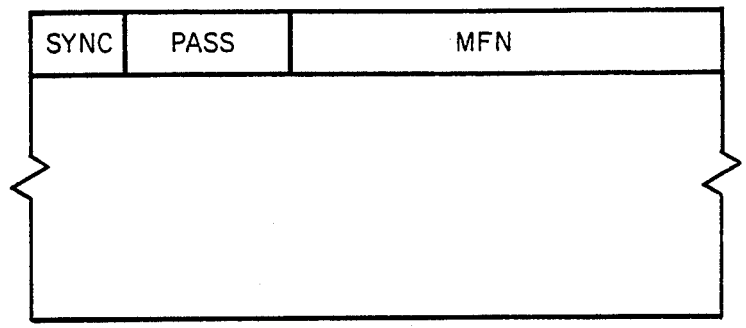
FIG. 18 illustrates a particular data format for use during the recognition step of the pattern recognition procedure in accordance with the invention.

In the recognition procedure, data is obtained specifically from two sources. First, the data generated as output data from the presort procedure (as shown in FIG. 17) is utilized by the recognition step of the pattern recognition procedure. Correspondingly, pattern definition data (previously stored in memory such as EPROM 744 illustrated in FIG. 12) is also utilized and compared with the previously described region output data from the presort procedure. If the comparison is successful, the appropriate color density data is extracted from the comparison. An exemplary embodiment of a specific configuration of pattern definition data is illustrated in FIG. 18. In this particular configuration, the measured field number (identified as MFN) essentially defines the placement position for the data extracted from this particular region. It should be noted that certain "special" cases may exist with respect to this data. For example, a particular configuration of the data may indicate an "ignored" region, where no data has been extracted. Correspondingly, another configuration may indicate the "nth" region which may be utilized for printer balance operations as explained in prior paragraphs herein.

The data identified as the PASS variable identifies a pass number for control strips requiring more than one pass. This pass number identifies the particular pass number in which this particular pattern region will be utilized. A particular data configuration can be utilized for control strips requiring only a single pass.

The variable identified as the SYNC variable defines the pattern region as being either a sync region or not a sync region. As previously described herein, the distance measurements for various regions following the sync region may be taken with respect to the position of the sync region. Accordingly, at least one sync region is preferably identified for each pattern definition. Further, the first sync region must be the first pattern region within the particular pattern definition.

Figure 19:
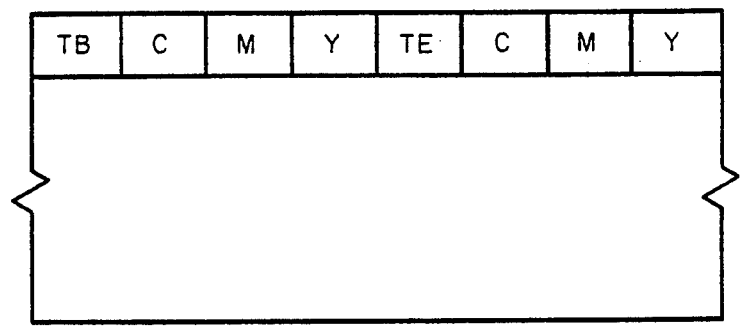
FIG. 19 illustrates an additional data format which may be utilized with the recognition step of the pattern recognition procedure in accordance with the invention.

A further variable utilized with the recognition procedure is illustrated in FIG. 19 and comprises a region color variable constructed by the recognition procedure. In this particular variable, the fields C, M, and Y, illustrated as the least significant bits in FIG. 19, indicate the particular recorded measured field colors. In the particular exemplary embodiment illustrated in FIG. 19, a set bit within these variables will cause the data for that particular color to be extracted from the measured region and stored in the color field selected by the variable illustrated in FIG. 18.

The variable identified as variable Te indicates the ending transition, while the variable identified as Tb indicates the beginning transition. When these variable are set to certain values, they indicate that the transitions of matching measured regions should be from darker to lighter or from lighter to darker.

The additional bits also identified as C, M, and Y may indicate a region color. Particular combinations of these bits may specify the dominant color of a matching measured region.

In addition to the variables illustrated in FIGS. 18 and 19, additional variables may also be utilized in the recognition procedure. For example, a variable identifying the length of a region, corresponding to the allowable size of a measured region, may also be defined. Correspondingly, allowable red, green and blue densities of a measured region may further be defined.

Figure 20:
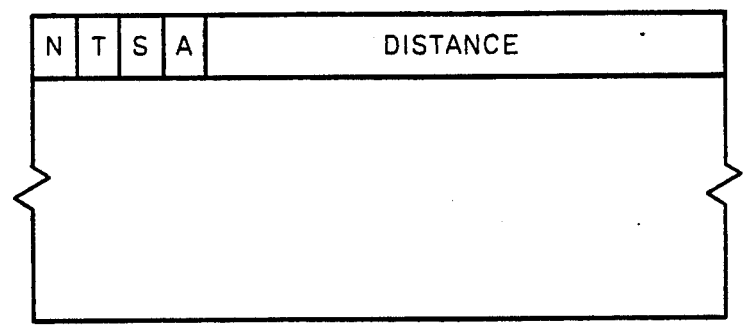
FIG. 20 illustrates a further data format which may be utilized with the recognition step of the pattern recognition procedure in accordance with the invention.

Still further, additional memory locations are required for defining a word value, corresponding to the distance from the previous region or the sync region. An exemplary embodiment of such data is illustrated in FIG. 20. More specifically, the variable identified as the distance variable may define a specific distance from the previous or sync region. Correspondingly, a bit defined as the A bit will define when the density measurements are taken from the raw data buffer, instead of a measured region buffer. The bit identified as the S bit may be characterized as the sync bit. When set, the position of the particular region can be calculated by adding the distance from the coordinates of the sync region. If the bit is cleared (corresponding to being set to zero), the position of the region can be calculated by adding the distance from the coordinate of the previous region.

The bit identified as the T bit is the transition bit. When set, a transition check should be made by the functional operations of the recognition procedure. When this bit is set to zero, transitions should be ignored. Correspondingly, the bit identified as the N bit will define whether the distance is a negative or positive distance.

Figure 13:
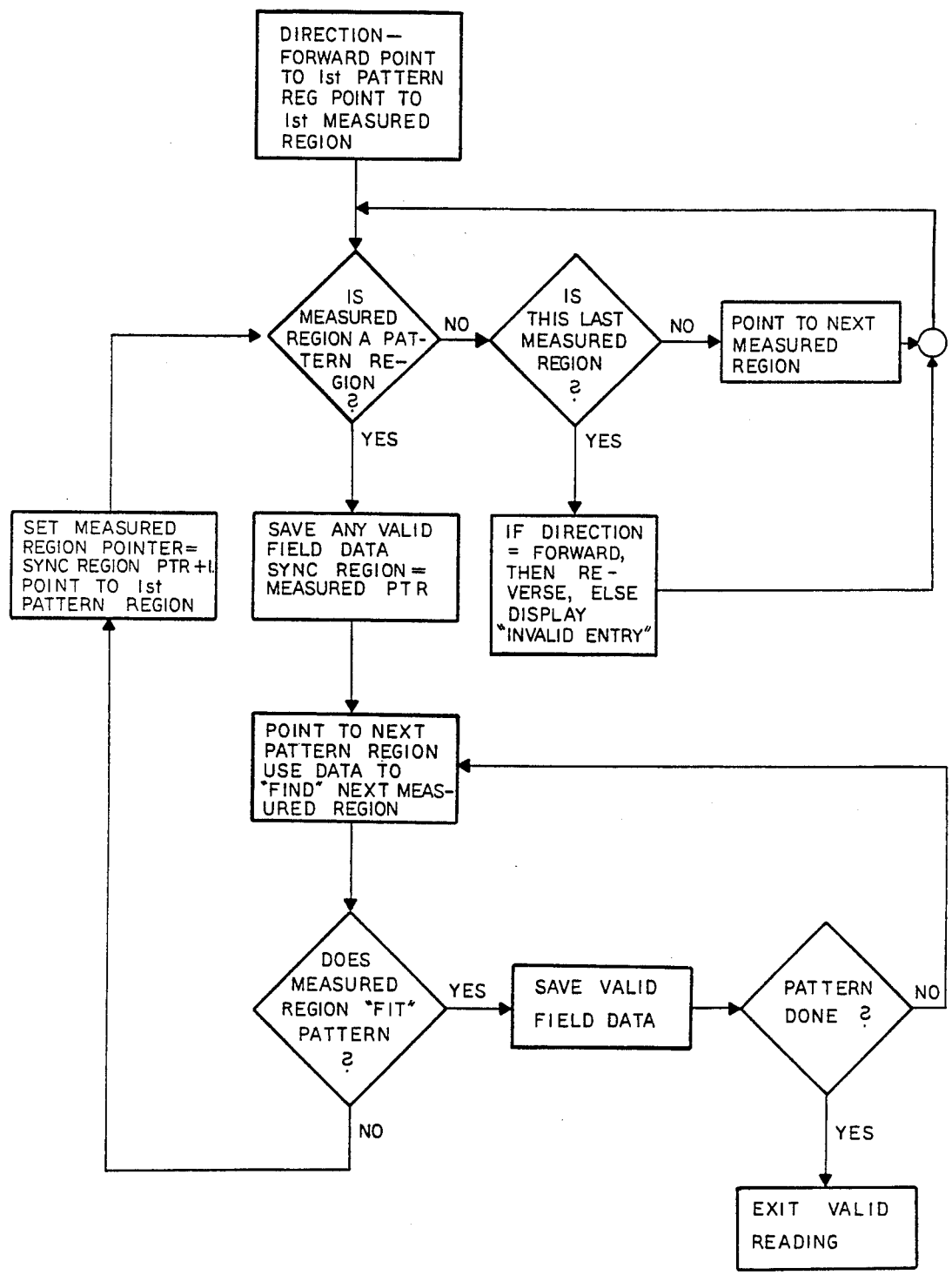
FIG. 13 is a sequence diagram illustrating certain functional operations associated with the recognition procedure for the pattern recognition procedure in accordance with the invention.

An operational sequence diagram associated with the recognition procedure is illustrated in FIG. 13. As shown therein, the sequence first "points" to the first pattern recognition point to the first measured region. A determination is then made as to whether the measured region pattern recognition exists. If not, a determination is made as to whether this is the last measured region. If this is not the last measured region, the pointer is incremented to the next measured region. If this is the last measured region, a determination is then made as to whether the direction for the then reverse pointer to the last measured region has been made. If so, a return is made to the functional sequence associated with the measured patter recognition.

If this is a measured region, appropriate valid field data are saved, and the sync region is set to the measured pointer. A "point" is then made to the next pattern recognition, and appropriate data is utilized to find the next measured region. If the measured region does not fit the pattern, the measured region pointer is set to the sync region pointer, incremented by one. A pointer is then made to the first pattern region. Thereafter, a determination is then made as to whether the measured region corresponds to the pattern region.

If the measured region fits the pattern, appropriate valid field data is saved, and a determination is made as to whether the pattern is completed. If not, the appropriate pointer is incremented to the next pattern region, and appropriate data is utilized to find the next measured region. If the pattern is complete, an exit of the sequence is made with an indication that a valid reading has been determined.

In accordance with the foregoing, the densitometer apparatus 210 can be utilized for purposes of performing various pattern recognition procedures associated with a comparison of control strips with previously stored data representing valid control strip tolerances. However, it should be emphasized that the principles of the pattern recognition procedure are not limited to the specific densitometer apparatus 210 described herein. In fact, the pattern recognition procedure can be employed with apparatus other than densitometers. Still further, the features of the pattern recognition procedures described herein and in accordance with the invention are not in any manner necessarily limited to three-color functions or to the use of the spectral filters described herein. A different number of colors and different color shades could be employed without departing from the novel concepts of the invention. It will be further apparent to those skilled in the art that additional modifications and variations of the above-described illustrative embodiment of the invention may be effected without departing from the spirit and scope of the novel concepts of the invention.

The embodiments of the invention in which an exclusive property or privilege is claimed are defined as follows:

1. A method adapted for use in a densitometer system for measuring color characteristics of object samples under test, said method directed to comparison of color data read from a control strip object sample with color data previously stored in a memory means of said densitometer system, said method comprising the steps of:

reading said control strip and storing data samples representative of color samples of said control strips;

storing with each of said data samples a distance measurement indicative of a position of each of said data samples;

formatting said data samples into a plurality of regions, each of said regions comprising a plurality of successive data samples having common parameters within predetermined tolerances;

comparing each of said regions with said previously stored color data; and generating an indication to an operator of said densitometer system whether said regions match or do not match said previously stored color data.

2. In a system for measuring color characteristics of object samples under test, said system comprising memory means for storing color pattern data representative of desired color characteristic data, reading means for reading an object sample and generating data signals representative of measured color characteristic samples of said object sample, processing means connected to said reading means for processing said data signals and storing in said memory means measured data samples representative of said data signals, the improvement wherein said processing means further comprises:

formatting means for formatting said measured data samples into a plurality of measured regions, each of said measured regions representing a plurality of said measured data samples having common parameters within tolerances;

comparison means for comparing said measured regions with said color pattern data; and indicating means for generating signals indicative of whether one or more of said measured regions match or do not match said color pattern data.

3. A system in accordance with claim 2 characterized in that:

said system further comprises position determining means connected to said processing means for generating position signals indicative of positions of said measured color characteristic samples on said object sample; and said processing means comprises means for storing, as part of each of said measured data samples, position data indicative of said position signals.

4. A system in accordance with claim 3 characterized in that:

said system further comprises motive means for automatically moving said object sample and/or said system relative to each other during reading of said object sample; and said position signals comprise information indicative of said relative movement.

5. A system in accordance with claim 2 characterized in that said color pattern data is stored in said memory means so as to define individual color pattern regions, and said comparison means compares said measured regions with said color pattern data by comparing said measured regions with said color pattern regions on a region-by-region basis.

6. A system in accordance with claim 5 characterized in that said color pattern data for each of said color pattern regions comprises data representative of size, predominant color characteristics, color densities, transitions and relative position.

7. A system in accordance with claim 5 characterized in that said color pattern data for at least certain of said color pattern regions comprises data defining whether a color pattern region is a SYNC region.

8. A system in accordance with claim 7 characterized in that said color pattern data for color pattern regions after said SYNC region comprises data representative of position relative to said SYNC region.

9. A system in accordance with claim 5 characterized in that said color pattern data for each of said color pattern regions comprises, for an object sample requiring a plurality of passes through said system, data representative of a particular pass number during which a color pattern region will be utilized for comparison.

10. A system in accordance with claim 5 characterized in that said color pattern data for each of said color pattern regions comprises data defining region size and color density characteristics, and data representative of allowable deviations of said measured regions from said region size and color density characteristics.

11. A system in accordance with claim 2 characterized in that said comparison means comprises means for comparing sizes of said measured regions with sizes defined for said color pattern data.

12. A system in accordance with claim 2 characterized in that said comparison means comprises means for comparing transitions of said measured regions with traNsitions defined for said color pattern data.

13. A system in accordance with claim 2 characterized in that said comparison means comprises means for comparing distances between said measured regions with positional data defined for said color pattern data.

14. A system in accordance with claim 2 characterized in that said comparison means comprises means for comparing predominant color characteristics of said measured regions with predominant color characteristics defined for said color pattern data.

15. A system in accordance with claim 2 characterized in that said comparison means comprises means for comparing color density characteristics of said measured regions with color density characteristics defined for said color pattern data.

16. A system in accordance with claim 2 characterized in that said formatting means comprises means for generating a set of measured region output data for each of said measured regions, said measured region output data comprising data representative of transitions, size, position and color characteristics.

17. A system in accordance with claim 2 characterized in that said reading means comprises means for reading said object sample in either of two opposing directions.

18. A system in accordance with claim 2 characterized in that:

said object sample comprises repeating color characteristic patterns;

said color pattern data is stored in said memory means so as to define an expected, repeating color pattern region; and said processing means comprises means for maintaining a count of the number of repeating color characteristic patterns found which match said repeating color pattern region.

19. A system in accordance with claim 2 characterized in that said formatting means comprises data sample comparison means for comparing color characteristics of successively obtained color samples.

20. A system in accordance with claim 19 characterized in that said data sample comparison means comprises means for defining, for purposes of formatting measured regions, allowable tolerances of measured color characteristics of a data sample as a function of measured color characteristics of another data sample.

21. A system in accordance with claim 2 characterized in that said reading means comprises:
light source means for generating light rays and directing said light rays onto said object sample;
filter means responsive to light rays from said object sample so as to discriminate predetermined color shade sets of spectral responses of said light rays from said object sample; and
detection means responsive to light rays transmitted through said filter means for generating said data signals as representative of the intensities of light rays transmitted through said filter means.

22. A system in accordance with claim 21 characterized in that said system further comprises motive means connected to said processing means for automatically moving said object sample through said system adjacent said light source means, so as to provide an automated measurement of a plurality of color patches associated with said object sample.

23. A system in accordance with claim 21 characterized in that said system further comprises guide means mounted to said system and adjustable by an operator of said system, so as to provide a guidance in at least one dimension of said object sample through said system.

24. A system in accordance with claim 21 characterized in that said filter means comprises reflection filter means positioned at a predetermined angle relative to the direction of object illumination by said light source means, and said reflection filter means is responsive to light rays reflected from said object sample so as to discriminate a predetermined color shade set of spectral responses of said reflected light rays.

25. A system in accordance with claim 21 characterized in that said filter means comprises transmission filter means positioned relative to the direction of object illumination by said light source means, and said transmission filter means is responsive to light rays transmitted through said object sample so as to discriminate a predetermined color shade set of spectral responses of said transmitted light rays.

26. A system in accordance with claim 2 characterized in that said system further comprises input means connected to said processing means for providing operator input to said system.

27. A system in accordance with claim 2 characterized in that said indicating means comprises display means connected to said processing means for providing visual displays to an operator, indicative of functions performed by said system.

28. In a system for measuring color characteristics of object samples, including a control sample, said system comprising at least one memory for prior storage of color pattern data representative of desired color characteristic data, a light source for directing light rays toward said object sample, filter apparatus for filtering light rays reflected from or transmitted through said object sample, detection circuitry for generating signals representative of intensities of said filtered light rays, and processing means connected to said detection circuitry for processing said signals and generating measured data samples representative of said signals, the improvement wherein said processing means further comprises:
means for generating each of said measured data samples with data representative of color characteristics and relative positions on said control sample; and
formatting means for evaluating said data representative of color characteristics and identifying measured regions, each of said measured regions representing a plurality of successive measured data samples, wherein color characteristic of at least two successive measured data samples fall within allowable deviations of each other.

29. A system in accordance with claim 28 characterized in that said processing means further comprises output data means for generating a set of output data for each measured region, wherein each set of output data comprises data representative of transitions, size, position and color characteristics for the corresponding measured region.

30. A system in accordance with claim 29 characterized in that said processing means further comprises:
means for storing said color pattern data so as to define individual color pattern regions, with color pattern data for each color pattern region comprising data representative of size, predominant color characteristics, color density characteristics, transitions and relative position; and
comparison means for comparing said sets of output data with said color pattern data on a region-by-region basis.

31. A method adapted for use in a system for measuring color characteristics of object samples under test, said method comprising the steps of:
storing color pattern data representative of desired color characteristic data;
reading an object sample and generating data signals representative of measured color characteristic samples of said object sample; and
processing said data signals and storing in a memory means measured data samples representative of said data signals;
characterized in that said method further comprises the steps of:
formatting said measured data samples into a plurality of measured regions, with each of said measured regions representing a plurality of said measured data samples having common parameters within tolerances;
comparing said measured regions with said color pattern data; and
generating signals indicative of whether one or more of said measured regions match or do not match said color pattern data.

32. A method in accordance with claim 31 characterized in that said method further comprises the steps of:
generating position signals indicative of positions of said measured color characteristic samples on said object sample; and
storing, as part of each of said measured data samples, position data indicative of said position signals.

33. A method in accordance with claim 32 characterized in that said method further comprises the steps of:
automatically moving said object sample relative to said system during reading of said object sample; and
generating said position signals in accordance with said relative movement.

34. A method in accordance with claim 31 characterized in that said storage of said color pattern data comprises storage so as to define individual color pattern regions, and said comparison of said measured regions with said color pattern data comprises comparison of said measured regions with said color pattern regions on a region-by-region basis.

35. A method in accordance with claim 34 characterized in that said color pattern data for each of said color pattern regions comprises data representative of size, predominant color characteristics, color density characteristics, transitions and relative position.

36. A method in accordance with claim 34 characterized in that said method further comprises the step of defining a SYNC region for said color pattern regions.

37. A method in accordance with claim 34 characterized in that said method further comprises the step of defining, for at least certain of said color pattern regions, data representative of a particular pass number during which a color pattern region will be utilized for comparison.

38. A method in accordance with claim 31 characterized in that said method comprises comparison of sizes, transitions, relative positions, predominant color characteristics and color density characteristics of said measured regions with comparable parameters defined for said color pattern data.

39. A method in accordance with claim 31 characterized in that said method further comprises maintaining a count of the number of repeating color characteristic patterns of said object sample which match a repeating color pattern region of said color pattern data.

40. A method in accordance with claim 31 characterized in that said method comprises defining, for purposes of formatting measured regions, allowable tolerances of measured color characteristics of a data sample as a function of measured color characteristics of another data sample.

* * * * *